(12) United States Patent
Patton

(10) Patent No.: US 11,771,649 B1
(45) Date of Patent: Oct. 3, 2023

(54) PHARMACEUTICAL LOTION OR SALVE UTILIZING MIXED METAL HYDROXIDE ANTIMICROBIAL CHARGED PARTICLES

(71) Applicant: Magalum LLC, Lake Jackson, TX (US)

(72) Inventor: Robert Thomas Patton, Lake Jackson, TX (US)

(73) Assignee: Magalum LLC, Lake Jackson, TX (US)

( * ) Notice: Subject to any disclaimer, the term of this patent is extended or adjusted under 35 U.S.C. 154(b) by 0 days.

(21) Appl. No.: 18/127,633

(22) Filed: Mar. 28, 2023

Related U.S. Application Data

(63) Continuation-in-part of application No. 17/490,269, filed on Sep. 30, 2021, now abandoned.

(60) Provisional application No. 63/188,635, filed on May 14, 2021.

(51) Int. Cl.
| | | |
|---|---|---|
| *A61K 9/06* | (2006.01) | |
| *A61K 33/08* | (2006.01) | |
| *A61K 47/38* | (2006.01) | |

(52) U.S. Cl.
CPC ............. *A61K 9/06* (2013.01); *A61K 33/08* (2013.01); *A61K 47/38* (2013.01)

(58) Field of Classification Search
CPC ........... A61K 9/06; A61K 33/08; A61K 47/38
See application file for complete search history.

(56) References Cited

U.S. PATENT DOCUMENTS

| | | | |
|---|---|---|---|
| 4,990,268 A | 2/1991 | Burba, III et al. | |
| 5,154,932 A | 10/1992 | Burba, III et al. | |
| 5,234,914 A * | 8/1993 | Gallina | A61K 45/06 |
| | | | 514/882 |
| 9,474,734 B2 | 10/2016 | St. Laurent | |
| 2012/0052052 A1 | 3/2012 | Xi | |

OTHER PUBLICATIONS

Reimer et al. Handbook of Formulating Dermal Applications a Definitive Practical Guide; Editor: Nava Dayan; Scrivener Publishing, Wiley Copyright: 2017; Chapter 2: pp. 29-30 and 42-43) (Year: 2017).*

MayoClinic Contact dermatitis, Jun. 19, 2020, 4 pgs., (from online retrived Jun. 15, 2022: https://www.mayoclinic.org/diseases-conditions/contact-dermatitis/symptoms-causes/yc-20352742?p=1, Jun. 19, 2020).

Merriam-Wester definition of salve(online retrieved on Jun. 14, 2022 from: https://www.merriam-webster.com/dictionary/salve#; 2 pgs., 2020.

\* cited by examiner

*Primary Examiner* — Ernst V Arnold
(74) *Attorney, Agent, or Firm* — Technology Law PLLC; Karen L Kimble

(57) ABSTRACT

This invention concerns a formulation of a hydrated mixed metal hydroxide and a nontoxic, non-anionic thickener, to form a salve or lotion which does cause synereses of the formulation. This formulation, when applied to a person or animal, forms a film that acts as an astringent, has antimicrobial palliative properties for many negative pathogens, burns, rashes and other skin maladies.

17 Claims, 12 Drawing Sheets
(12 of 12 Drawing Sheet(s) Filed in Color)

80% CVSHealth Antiseptic Skin Cleanser, 20% MMOI

PHARMACEUTICAL LOTION OR SALVE UTILIZING MIXED METAL HYDROXIDE ANTIMICROBIAL CHARGED PARTICLES

FIELD OF THE INVENTION

The present invention concerns a pharmaceutical salve or lotion made from positively charged particles of crystalline mixed metal hydroxide compounds and an aqueous, non-anionic thickener.

BACKGROUND OF THE INVENTION

There is a perceived need for materials which are an astringent agent, an anion exchange agent, and an antimicrobial agent that are useful for treating conditions caused by negatively charged conditions that occur to animals, including humans. Such conditions can be caused by a diverse number of events, for example pathogens, rashes, burns, blisters, insect stings, marine animal stings, contact dermatitis, and wounds. Yet such materials are substantially innocuous to animals and persons when applied topically.

It is known that certain hydrated metal compounds, such as $AlOCl \cdot nH_2O$ (pH about 5 or less) or the like, used in underarm deodorant formulations, are said to prevent or abate the growth of bacteria. Nevertheless, there are relatively few commercial products and uses where the active ingredient alone is an inorganic composition of mixed metal hydroxides.

However, there was a development of inorganic compositions by Dr. John Burba for purposes as drilling fluids used in oil wells or for oil extraction, which was a business of his employer, The Dow Chemical Company. Although Burba discloses the fact the particles were antimicrobial, he does not teach how the particles could be made into a useful lotion or salve, although he alleges such use. When such salves or lotions are tried to be made, it was found that this was not very simple to accomplish as Burba failed in those attempts. Burba does mention two formulations which he may have considered as salve candidates, one being the hydrated form of MMOH and the other being the adduct of the hydrated MMOH with bentonite. However, these do not work successfully as shown in the comparative discussion of this application. Burba does not disclose other useful properties for these particles and he does not disclose the use of a thickener.

Although the present formulation has many benefits, prior to this invention no commercial products for pharmaceutical or cosmetic uses have been developed using MMOH, a thickener and water, with no other ingredients required or added. In the above cited patents by Burba, he tried a few thickeners, but because he did not understand how these microcrystals worked for such uses, they all failed to make a salve or lotion. At that time, Burba's focus was on drilling fluids in the oil well drilling industry. It has been 35 years since the MMOH microcrystals were made by Burba, but no one who has studied this art has understood how to make any useful salve or lotion.

The following patents by Dr. John Burba (hereinafter collectively Burba) were developed using mixed metal hydroxides, which were intended to be used mainly as drilling fluids to carry oil field fines because of their rheology and viscosity.

U.S. Pat. No. 5,154,932 (Burba) describes positively charged mixed metal hydroxide (MMOH) crystals which have antimicrobial properties with the best pH range above 8. It teaches that these crystals can be used in lotions, medicinal creams, disinfectants, mildewcides, and fungicides. It mentions that the use of ammonium hydroxide produces multilayer crystals. It tests the antimicrobial property against *Pseudomonas aeruginosa* (ATCC #15442), *Staphylococcus aureus* (ATCC #6538), *Escherichia coli* (ATCC #11229), *Candida albicans* (ATCC #10231), and *Aspergillus niger* (ATCC #16404). It was found to be effective against everything but *Aspergillus niger* where it was only somewhat effective. It teaches that the most effective crystals are monolayer and that the crystals interact with bentonite, which is used for oil field drilling fluid. No thickener is present.

U.S. Pat. No. 4,990,268 (Burba) describes the beneficial interaction of the MMOH crystals with bentonite clay, which is the principal component of oil field drilling fluid. It defines the attributes of the drilling fluid and the changes imparted to the bentonite drilling fluid by the addition of the crystals. The process disclosed for making the MMOH is a flash precipitation technique to prepare the gelling agents, and closely approximates a steady state reaction wherein the ratio of reactant feeds (cations/anions), and other reaction conditions (e.g. concentration, pH, temperature) are substantially constant.

As is evident from the discussion above, a better formulation for a salve or lotion is needed to provide topical application for the variety of uses now envisioned and tested.

BRIEF SUMMARY OF THE INVENTION

There is a perceived need for a salve or lotion utilizing positively charged crystalline particles in order to effect certain pharmaceutical attributes. This salve should have the antimicrobial properties of the particles, but would also be nontoxic, have ion exchange properties, analgesic properties, astringent properties and wound healing properties attributable to the crystalline particles as an adduct with a thickener. Additionally, the salve or lotion would have a pH suitable for application to open wounds without causing pain to the animal or destroying the adduct, have astringent film forming ability that protects any open wounds, have a good hand-feel e.g., non-gritty, smooth application, and not separate into phases upon standing.

This invention provides a formulation of hydrated mixed metal hydroxides in a salve or lotion or diluted lotion having an aqueous, non-anionic thickener which can form an adduct with the MMOH crystal lattice to provide these desired properties. The present formulation acts as an antimicrobial for treatment of various infections, such as bacterial, viral, yeast, and fungal infections, as a palliative for insect stings, e.g. fire ant stings, bee stings, wasp stings, marine animal stings, e.g., jelly fish stings, wounds, rashes, burns, and lesions, e.g., shingles, blisters, open wounds from an injury, chiggers, mosquitos and other skin maladies and as a preventative to keep wounds, rashes, burns, and lesions from becoming reinfected. The present formulation is effective for many skin maladies, for example against microbes such as germs, viruses, bacteria, fungus, yeast, or any other microscopic organism which has a negatively charged surface. It is thought this formulation can block the effect of such pathogens, allergens and skin irritations by rendering or changing the surface charge from negative to neutral or positive and thereby prevent the mechanism from infection through a cell well from happening.

There are three components of this present formulation; namely, the hydrated mixed metal hydroxide; a non-anionic, nontoxic thickener; and water. The formulation is thus aqueous as its base without any other typical oils for salves or lotions present. Each of these components will be discussed further below. The entire formulation is described by the following.

A formulation consisting essentially of a mixed metal hydroxide, MMOH, of the formula

$(Li)_z D_d T(OH)_q (A^{-1})_y \cdot xH_2O$   Formula (I)

wherein:
  D is a divalent metal of Mg, Ca, Zn, Mn, Co or Ni;
  d is 0.8 to 1.1 and can be other than an integer;
  T is a trivalent metal of Al or Ga;
  A is an anion of Cl, Br, F or I;
  y is 0 to 0.4, and can be other than an integer;
  q is 4.6 to 5.7, and can be other than an integer;
  z is 0 or 1, and can be other than an integer;
  $xH_2O$ is water of hydration, entrapped or associated with the MMOH crystal lattice, where x is from 6 to 100;
with an aqueous, non-anionic, nontoxic thickener, which does not destroy the crystalline structure of the MMOH, selected from Cellulosic thickeners, copovidone, hydroxypropyl cyclodextrin, native cyclodextrin, corn starch or egg white,
wherein the ratio of MMOH to thickener is about 2/3 by wt. MMOH to 1/3 by wt. thickener,
to form an aqueous, nontoxic adduct as a salve or lotion that is resistant to syneresis.

The MMOH particles do not agglomerate or separate into 2 phases in the salve or lotion. When applied, the salve or lotion forms a film that is astringent, durable to cover the affected area and keep it clean from other infections often without other bandages needed.

This formulation has no other components present or any additives needed to obtain the desired results. Only minor or trace amounts of other components are present such as by-products from making the formulation or its components. It is surprising to find a formulation that is dependent on inorganic crystals to be effective in a salve or lotion. This feature is unique compared with other commercial salves or lotions used for these purposes.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These color drawings are needed to enable the distinctions of the various conditions to be clearly seen.

FIG. 6 has FIGS. 6A-D that are photographs of a salve of Example 4 used over time to treat a horse in Example VIII.

FIG. 7 has two photographs.

FIG. 11 has two photographs.

DETAILED DESCRIPTION OF THE INVENTION

Figure 1:
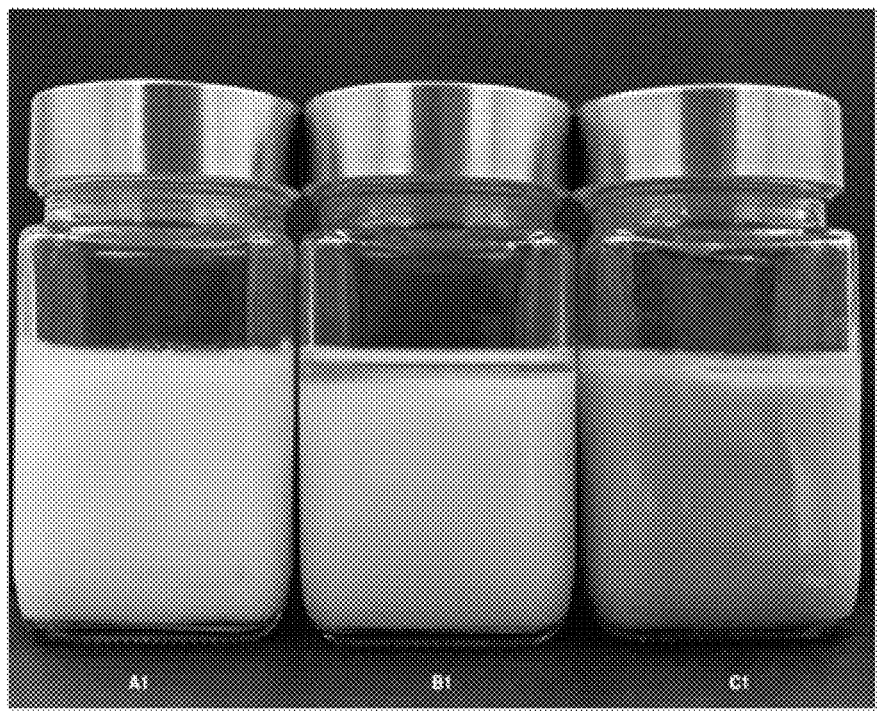
FIG. 1 has three vials as A1-C1 that are photographs taken on Feb. 10, 2022 of salves made by the procedure of Burba and the present invention. FIG. A1 is the present invention, Example 10; FIG. B1 is Burba's MMOH with water addition, Comparative Example A; FIG. C1 is Burba's MMOH with bentonite addition, Comparative Example B.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary base means NaOH, KOH or $NH_4OH$

Cellulosic thickener means cellulosic polymers having alkyl groups selected from methyl, ethyl, a mixture of methyl and ethyl, hydroxypropyl, and hydroxyethyl and includes HPMC, MC, HEC, EC, MHEC and HPC. Carboxyl groups are excluded from such cellulosic structures, including carboxymethyl cellulose (CMC). The maximum molecular weights are 1,200,000 for HPMC, 1,300,000 for HEC, 200,000 for HPC, and 220,000 for MC.

cm means centimeter(s)

cool water means about 32 to about 45° F. water or about 0 to about 7° C.

*E. coli* means *Escherichia coli*

EC means ethyl cellulose g mean gram(s)

hot water means from about 190 to about 212° F. or about 88 to about 100° C.

HEC means hydroxyethyl cellulose; the MW at the high end is 1,300,000.

HPC means hydroxypropyl cellulose, the MW at the high end is 200,000.

HPMC means hydroxypropyl methylcellulose; preferably RT water dispersible HPMC; the MW range is high end from about 200,000 to 1,200,000; the MW for low end is below 200,000

Kg means kilograms(s)

L means liter(s)

MC means methylcellulose, the MW at the high end is 220,000.

MHEC means methylhydroxyethyl cellulose mL means milliliter(s)

MMOH means crystalline mixed metal hydroxide compounds as defined herein by Formula (I)

RT means room temperature or ambient temperature, about 18 to about 26° C., or about 65 to about 80° F.

Thickener(s) means a non-ionic thickener selected from Cellulosic thickeners, copovidone, hydroxypropyl cyclodextrin, native cyclodextrin, corn starch or egg white % wt. means percent by weight

DISCUSSION

It is known that certain mixed metal hydroxides (MMOH) are of layered crystalline structures that exhibit cationic surface charges. Burba indicated some MMOH structures have antimicrobial properties which might enable formulations to be made that would be effective for the treatment of certain animal and human diseases. Some examples are found in U.S. Pat. Nos. 5,154,932; and 4,990,268, both by Burba, as discussed above.

Nonetheless, a method of making salves or lotions utilizing these mixed metal hydroxide particles has not been known, nor have the properties of such salves or lotions been known or proven.

The present formulation requires only three components; namely, an MMOH from Formula (I), a specified non-anionic thickener having specific properties, and water, No other components are present in a significant amount. A few additives might be added in very limited amounts providing they do not interfere with the MMOH charge and properties.

This finding of such specific three components to make the present formulation were not known previously. Many persons have tried as persons skilled in this art have known of these MMOH crystals for greater than 30 years. Other attempts to make these types of formulations have failed. The presently claimed formulation has been the only combination that achieves the desired results and surprisingly with only three components.

In contrast, many known salves and lotions require the presence of additional ingredients to achieve the effects of the present formulation. Such additives have been found for this present formulation to be unnecessary and in fact can be detrimental by: a) causing phase separation of the salve or lotion, b) inferring with the positive charge required for the MMOH microcrystalline particles in the formulation, c) interfering with the film formation of the formulation on drying, d) having a gritty or bad hand feel on use, and e) not adding any benefit to the animal, including humans, in the results obtained while increasing the costs to make it.

Turning to specifics on each component of the present formulation.

Water

Any type of water can be used so long as it contains no toxic ingredients and only low amounts of any ionic compounds such as salts that could interfere with the MMOH charge. The formulation and lotion are aqueous systems so that the MMOH and the thickener must be able to be either soluble, suspended, a slurry or compatible with such aqueous environment. The water must retain the other two components without causing phase separation.

Also, the MMOH used has waters of hydration present meaning water ionic or otherwise entrapped or bound within or on the surface of the MMOH crystals. Thus, water within the MMOH crystals or on its surface, whether entrapped or loosely bound, are available to the formulation. Those waters of hydration are also released during drying of the film formed by the formulation and must be accounted for in the overall fluid present in the present formulation. The amount of water added in the present formulation is from about 15 to about 35% w.; however, if the water of hydration from the MMOH is included as water then the total water present in the formulation is from about 90 to about 96% wt. The resulting salve or lotion has a viscosity required to be applied as a salve or lotion without separating into two or more phases.

MMOH

The hydrated microcrystals of Formula (I) as shown above and in the present claims represent the MMOH component of the present formulation. Because these are inorganic compositions, they behave very differently from organic molecules for this purpose. Some the issues presented are difficult to overcome.

Syneresis—Phase Separation

To better understand this complex area of inorganic chemistry an understanding of syneresis is required. One half of the active ingredient in a desired salve of the present formulation is a crystal lattice having Magnesium, Aluminum, Hydrogen, and Oxygen, as one MMOH within claim 1, Formula (I). This lattice is very similar to the structure of the mineral, bentonite. There are a great many references to the formation and chemistry of a crystal lattice, for example, an article *The Colloidal and Rheological Properties of Bentonite Suspensions* by Paul F. Luckham and Sylvia Rossi, Dept. of Chemical Technology, Imperial College, Prince Consort Road, London SW7 2BY, gives the best overall description of the chemistry involved.

The microcrystals described in this present application consist of minute particles of a crystal lattice which have a positive surface charge on the flat surfaces and a negative charge around the edges. It could also be said that they have a more concentrated electron density on the edges and an electron deficiency on the flat surfaces. Because of the attraction of opposite charges, these microcrystal particles normally have a strong tendency to arrange themselves in a configuration approximating a house of cards with the flat surfaces perpendicular to the edges of adjacent microcrystal particles. This arrangement is called an edge to face dispersion. This edge to face tendency has made the aqueous slurry of such microcrystal particles valuable as a thickener with some unique properties and some drawbacks.

Thus, the MMOH can be viewed as a first thickener in the formulation. In the concentrated form of hydrated MMOH particles, which has been marketed as a thickener, the product initially contains many waters of hydration. Much of this water is trapped in the spaces that can be visualized as the voids in the house of card structure. However, because of this feature, a deficiency in the thickener application of these microcrystal particles appears because of the necessary attraction effected between flat surfaces and edges. Depending upon pH and ion concentration in the aqueous media, it is also possible for the particles to configure themselves in an edge to edge, a face to face configuration, or a completely dispersed configuration. In all of these additional configurations, the entrapped water molecules are greatly reduced, particularly in the completely dispersed configuration. This is the reason for the great release of water from the crystal lattice when the second thickener (the thickener claimed) that acts like a dispersant is first added.

The salve formulation of the present application utilizes these microcrystal particles. Additionally, it should be pointed out that the surface charge of the flat plates changes as the configuration of the crystal lattice changes. The efficacy of the particles as a pharmaceutical depends upon the dispersion. Anything that changes the nature of the dispersion changes the performance of the salve formulation.

Unfortunately, the microcrystal particles have a strong tendency to coalesce into one of the less efficient configurations, giving up waters of hydration in the process. The visible effect of this rearrangement is a phase separation of the thickener into a concentrated microcrystalline slurry on the bottom with a pure water phase on the top. This phase concentration phenomenon is called syneresis. Photos of this effect are provided FIGS. 1-3 and discussed later in this application.

Since syneresis imparts bad properties to a pharmaceutical salve or lotion, this property of the microcrystal particles has to be somehow overcome in order to use the microcrystals as the active ingredient in a salve or lotion. In order to formulate the microcrystals into a usable salve or lotion, it is necessary to separate them from each other and hold them dispersed in the resulting slurry. If the microcrystals were marketed in the original form without the addition of the thickener, the microcrystals would forever be subject to continual, repeated phase separations, each reducing the efficacy of the incomplete dispersion of microcrystals for the intended pharmaceutical uses and each creating a very negative salve customer response.

In order to prevent this syneresis, a second thickener (MMOH is a thickener itself) was added to the original microcrystal product. This second thickener (the thickener claimed as a component of the formulation) has to fulfill the function of microcrystal separation and suspension agent without being the cause of exacerbated phase separation. This is a daunting task.

The claimed thickener consists of long chained molecules which accomplish this thickening task by entanglement with one another and usually some attraction of electron rich portions of the thickener molecule with electron deficient portions on an adjacent thickener molecule. If the electron rich portions of the thickener molecule are too strong in charge, the molecules of thickener become attached to the electron deficient portions of the microcrystals with hydrogen bonding and this causes coalescing of the crystals and resulting worsened syneresis.

On the other hand, if the electron rich portions of the thickener molecule are too weak in charge, then the attraction of the electron rich portions of the microcrystal becomes attached to the electron deficient portions of the thickener molecules by hydrogen bonding causing coalescing of the crystals and resulting worsened syneresis.

Thus, the attraction of one thickener molecule (MMOH) to another thickener molecule (the added thickener) needs to be almost exactly the same as the attraction of one microcrystal to another microcrystal. If the electron density is over weighted in either direction, the dispersion fails. Because of that sensitivity, viscosity alone overcomes effects caused by differing electron density and the microcrystals are separated and suspended indefinitely. The property of the added thickener thus has to be extremely specific. Otherwise, what it might affect by suspension is overcome by attraction. This is why the list of thickeners has been added to claim 1 to clarify what ones can function for this purpose.

Interestingly, it is this phenomenon that makes the identification of an ideal second thickener difficult. Starting with concentrated MMOH, which already shows signs of syneresis, as a thickener is added to the MMOH, the first result observed is that the viscosity goes down because of the waters of hydration that are released from the MMOH dilute the mixture. Only after most of the waters of hydration have been released, does the reverse effect occur and the mixture starts to increase in viscosity. This thickening continues with additions of the second thickener until ultimately, if the added thickener is uniquely effective, signs of syneresis disappear. This need for significant amounts of a second thickener is contrary to conventional thinking.

In addition to the effect of the added thickener related to its viscosity, the thickener and any accompanying compounds such as surfactants can change the properties of the thickener considerably. For instance, it is known that anionic surfactants should be avoided because of their contribution of undesirable anions to the microcrystal particles which get some of their properties from their ion exchange capacity. It is also known that nonionic surfactants should be avoided because of their tendency to change the efficacy of the particles by depositing on the flat surfaces through van der Waals forces. Because this tendency is related to the length of the hydrocarbon chain portion of the non-ionic surfactants, it is also related to the length of any hydrocarbon chain portions of the thickener chosen to also function as a dispersant. Further, it is known that the concentration of sodium and chloride ions in the dispersant thickener can considerably change the strength of the edge to face orientation and resulting incorporation of waters of hydration. Clearly, it is not a simple task to understand all these interactions and select the proper MMOH and thickener to use in combination. Claim 1 is directed to a select group for which these interactions have been found possible.

Syneresis is so important to the microcrystal dispersion that the very few really effective thickeners are vital ingredients in the formation of effective salves. A salve becomes more and more effective as the microcrystal particles are uniformly separated. The effect of a face to face or an edge to edge orientation of the microcrystal particles effects a reduction in both the entrapped waters of hydration and the adsorbed waters of hydration and thus the pharmaceutical performance of the dispersion. For this reason, each combination of each effective thickener with the right MMOH crystals needs to be recognized as a unique pharmaceutical with its own particular positive properties. Thus, all of the formulations now claimed will function for pharmaceutical uses but selection of each component as an aqueous salve must be thought through. Even if the electron attraction problems are overcome, the properties of the desirable thickeners still impart differences to the resulting salves. Thus, claim 1 has a subset of MMOH possible that can function in this manner—restricted from the broader group described by the cited Burba—to use for this purpose and a select group of thickeners.

A change in thickener composition for the MMOH salve results in just as big of change in performance as a change in chemical composition does to the organic chemical based salve. The claimed thickeners facilitate the formation of salves that dry to films with more tensile strength, more durability, more clarity, more cooling effect, encapsulate allergens with more efficacy, incorporate more water and thus impart more palliative effect as they dry, and impart more drying effect to the underlying epidermal tissue as they dry. Thus, these thickeners form adducts with the MMOH crystals and cause the formulation to have these properties.

Each combination of a different effective thickener with each different MMOH as shown in claim 1 produces a much more efficacious salve in some properties than either the original MMOH product by Burba without an added thickener or the adduct of the original MMOH slurry with bentonite (tried by Burba). Neither of which original or adduct product by Burba can truly be called a salve as the syneresis was still present. Much experimentation was required to find those thickeners that would accomplish the results needed.

To clarify, this present claimed formulation, the hydrated MMOH with the listed thickeners in an aqueous medium is the actual salve. No other salve or salve components are used. If the hydrated MMOH were to be added to an existing salve or salve formulated base, then it would not work because the microcrystals would be disrupted as explained above. It would not succeed for this intended purpose to make the presently claimed salve which has none of these extra additives or salve components. The reasons are that most known salves have lipophilic components which are not possible to use with MMOH. Burba could not make a salve by adding his anhydrous MMOH to a known salve. The concept was tried and resulted in no salve being formed (see FIGS. 8-10). The hydrated MMOH cannot be emulsified with other salve components as the crystal structure is destroyed for the above reasons. The anhydrous MMOH added to a known salve will remain as a powder, like sand, in the initial salve dispersion and contribute nothing to the properties of the salve. The hydrated MMOH will not disperse into a lipophilic salve base (which the vast majority of salve bases include).

Anhydrous MMOH will not go into the blood stream because it is an insoluble, inorganic solid that does not diffuse into the blood stream. Burba never used the hydrated MMOH in his proposed salve or lotion because he dehydrated his filter cake with the addition of glycerin to enable later rehydration. It is not the same MMOH as this formulation. They behave very differently in an aqueous environment. Burba's mixture of anhydrous MMOH could not be used for the present methods, as it does not provide these same properties as in the formulation with the present thickener. Data on this point is provided in the examples. Because Bura's mixture does not have these properties as the present formulation, it is not a question of inherency of the two MMOH compounds as they are starkly, significantly different (FIGS. 4 and 5). As an analogy to try to provide some clarity, consider that the R and S isomers of the same organic compound have very different activity as a pharmaceutical. In this case, the anhydrous and the hydrated form of MMOH are also very different compounds. The anhydrous MMOH by itself (Burba) or added to a known salve base does not provide the currently claimed properties and permit the method results. Burba's anhydrous MMOH added to any existing salve would have components present other than just a thickener. A salve base would not have only HPMC (as an example) in the jar to which Burba's MMOH could be added. Any of these extra components would likely disrupt the microcrystal of the MMOH and make it ineffective. The present hydrated MMOH is required to get the claimed results. Claim 1 has only hydrated MMOH. Anhydrous MMOH is a solid cake or powder which is very difficult to disperse in an aqueous media as it acts like sand. In contrast, hydrated MMOH is about 91% wt. of water and is a crumby solid of these various crystalline lattice structures discussed above. (FIGS. 4 and 5)

Although it would not seem likely that one would add a thickener to a thickener, that is what is done. Additionally, the viscosity of the first thickener (MMOH) goes down, not up, when the second thickener solution is added in sufficient quantities. At some point a stable dispersion is obtained. The fully hydrated MMOH is an easily crumbled solid which actually contains approximately 91 percent water. In spite of the high water content, a thickened water solution, which is approximately 98 percent water is added to the MMOH in order to disperse and suspend the microcrystals. The thickened water solution is used rather than trying to add a powdered solid thickener to the MMOH, which is at this point a solid. As one would deduce, it is very counterintuitive to add this thickened water to the MMOH. When the thickened water solution is mixed in, a salve with good viscosity, good appearance, and good pharmaceutical properties is produced. The salve of Example 1 contains about 67% wt. of hydrated MMOH. The resulting salve after adding thickener contains approximately 93% wt. water. Naturally, it is very hydrophilic. It is cooling when applied to the skin and when it dries, loosing so much of its volume, it shrinks, and containing the right thickener leaves a relatively strong film containing the active MMOH.

One considered alternative to a thickener is an emulsifying agent. A mixture of an emulsified hydrocarbon and MMOH is not stable from separation into phases. Separation always occurs because of the interaction of the emulsification agent with the MMOH. Thus, an emulsifying agent is not a replacement for the thickener.

In general, Burba's attempts to form a salve failed for several reasons. Anhydrous MMOH that he used is a solid that is very difficult to disperse. Burba had to add glycerin to get it to begin to disperse in a bentonite slurry. The present formulation does not add any glycerin. In contrast, the hydrated MMOH as used in this present invention is not stable and changes crystal lattice structures readily, which in turn results in phase separation. For this reason, adding a thickener stabilized this microcrystal suspension. The presence of such thickener is required in this present invention to allow the hydrated MMOH to stabilize in the dispersed form and produce the desired results.

Knowing how to overcome this phase separation issue is not a simple matter as Burba could not do it upon trying. An issue is the selection of a thickener which would not interfere with the desired charge of the MMOH, while still maintaining the needed viscosity of the salve to minimize syneresis.

Water of Hydration

The compounds of Formula (I) are all believed to be effective for the stated uses based on the theory of how these MMOH formulations accomplish the desired effect. The preferred compounds of Formula (I) are those where z is 0; D is Mg; T is Al; A is Cl. Especially preferred is Mg-Al(OH)$_{4.7}$Cl$_{0.3}$·34H$_2$O. Thus, these MMOH particles of Formula (I) have a significant amount of water of hydration present. Such water can be present on the surface of the MMOH particles or within the layers of the crystal lattice of the hydrated MMOH.

The waters of hydration are given up by the MMOH particles rather easily but added back or absorbed slowly. The presence of D and T cations causes diffusion to occur. The water wants to go to areas of the maximum ion concentration and to the places on the crystal that desire such water of hydration. The crystal of MMOH has a positive surface charge. These properties provide the astringent property of the formulated MMOH salve or lotion.

Manufacture of the Microcrystalline Dispersion

The positively charged microcrystals of Formula (I) are made by the following general procedure, which is a variation of the process described in U.S. Pat. No. 4,990,268 (Burba), incorporated by reference. A dilute aqueous solution of the metal salts is prepared, a dilute aqueous solution of the reagent base is prepared, and then streams of the two solutions are mixed in a mixing tee which accomplishes the conversion of the metal salts into the crystals almost instantaneously. The crystals formed are multilayer platelets which measure about 500 angstroms across the flat surface. The flat surface has the positive charge. In order to minimize the crystal size, the concentration of the two solutions must be kept low.

Any of several reagent bases may be used to accomplish the reaction and include sodium hydroxide, potassium hydroxide, ammonium hydroxide, and others. There seems to be no particular benefit of using one of these reagent bases over another with regards to the product being made. The relative costs of the reagents favor the selection of sodium hydroxide or ammonium hydroxide. For ease and safety of handling, ammonium hydroxide is preferable to sodium hydroxide.

Figure 4:
FIG. 4 is a photograph of a MMOH filter cake as a stiff, fragile, solid. It is anhydrous and thermally dehydrated to only 22.43 g from a 300 g hydrated sample.
Figure 5:
FIG. 5 is a photograph of a MMOH as a soft solid phase and somewhat sticky. It is fully hydrated and shown as a 300 g sample. When dried, it formed the anhydrous solid of FIG. 4.

Once the crystals are made they exist in an aqueous slurry containing the byproduct salt made in the process of removing the halide anions, usually chloride, from the two major metal cations. The crystals are recovered from the salty aqueous solution by a process of filtration. This produces a filter cake which is washed by passing deionized water through the cake. The washing step removes both the soluble salt and any excess reagent base or metal salt from the cake. The filter cake first exists as a stiff, fragile, somewhat sticky solid (FIG. 4) which, from a process standpoint, is difficult to handle. This filter cake gradually "relaxes" over a period of one day or more into two phases (e.g., expels water), one a liquid aqueous phase, and the other a soft solid phase (FIG. 5). FIG. 4 is the anhydrous MMOH and FIG. 5 is the hydrated MMOH of Formula (I).

The amount of MMOH in its hydrated form present in the salve is from about 50 to about 80% wt.

Thickeners

It has been found that it is necessary to have a specific thickener present with the MMOH. Because MMOH is itself a thickener, adding a second thickener is counterintuitive. However, adding more of the MMOH does not suffice to stabilize the dispersion of MMOH particles or prevent synereses.

The specific thickener serves more functions than viscosity control. The thickeners form a adduct with the MMOH crystals thereby facilitating the formation of a continuous film which has excellent adherence to the skin and is a palliative which reduces pain and makes itch go away, it has better astringency, better continuity, better transparency, better durability, and a better antimicrobial nature. Furthermore, the film forms a protective antimicrobial barrier over wounds relieving the necessity to use a bandage.

Not just any thickener will work such that the thickener selection can only be understood when the theory of the entire formulation is understood. Many thickeners have been tested as shown in the tables below. The ones tested had to be nontoxic and food grade. The various columns have the following meanings:

1=amount of hydrated MMOH, wt. %
2=additional water needed wt. % for the formulation in addition to the waters of hydration or free water associated with the hydrated MMOH
3=amount of thickener, wt. %
4=syneresis-disruption the delicate dispersion in such a way as to exacerbate the phase separation.
5=the ion exchange of the MMOH by introducing certain anions such as carboxylic ions into the aqueous media.
6=color and salve consistency e.g., soft (salve), applesauce (mixed gel), hard gel (stiff solid gel), and hand feel.

The various thickeners were selected as usual food additives that are known to thicken, readily available, nontoxic, and have some characteristics that might make them suitable for the present formulation as the thickener.

TABLE 1

Comparative Thickeners

| Thickener | 1 | 2 | 3 | 4 | 5 | 6 |
|---|---|---|---|---|---|---|
| Agar | NA | Solubility issue | NA | NA | No | Clear/hard/bad |
| Arrowroot | 78.01 | 17.49 | 4.5 | yes | no | Clear/soft/bad |
| Carrageenan | 66.67 | 32.32 | 1.01 | yes | yes | Clear/soft/good |
| Chitosan | NA | Required < pH 7 | NA | NA | yes | NA/NA/NA |
| Gellan gum | 66.67 | 32.4 | 0.9 | yes | no | Clear/hard/bad |
| Gelatin | NA | Gelled solid | NA | NA | no | NA/hard/NA |
| Guar gum | 66.67 | 32.8 | 0.53 | yes | no | Yellow/soft/bad |
| Gum arabic | NA | Solubility issue | NA | NA | no | NA/soft/NA |
| Xanthan gum | 66.67 | 32.48 | 0.85 | yes | no | Clear/soft/bad |
| Konjac | NA | Forms hard gel | NA | NA | no | NA/hard/NA |
| Locust bean gum | 66.7 | 32.3 | 0.73 | yes | no | Yellow/soft/bad |
| Pectin | NA | Solubility issue | NA | NA | no | NA/NA/NA |
| Tragacanth | 66.67 | 31.89 | 1.45 | yes | no | Clear/hard/good |

TABLE 2

Thickeners of this present formulation

| Thickener | 1 | 2 | 3 | 4 | 5 | 6 |
|---|---|---|---|---|---|---|
| Egg white | 94.3 | 0 | 94.3 | yes | no | Ivory/soft/good feel |
| HPMC K200 | 66.67 | 32.72 | 0.61-0.73 | no | no | Clear/soft/good feel |
| HPMC K 100 | 66.66 | 32.59 | 0.74-0.89 | no | no | Clear/soft/good feel |
| HPMC K 35 | 66.66 | 32.37 | 0.97-1.08 | no | no | Clear/soft/good feel |

TABLE 2-continued

Thickeners of this present formulation

| Thickener | 1 | 2 | 3 | 4 | 5 | 6 |
|---|---|---|---|---|---|---|
| MC A4M | 66.67 | 31.82 | 1.52-2.42 | no | no | Clear/soft/good feel |
| Corn starch | 66.67 | 31.31 | 2.02-66.87 | yes | no | Clear/soft/good feel |

The salve viscosity and salve texture were all good for the thickeners of this present formulation in Table 2. Other thickeners are possible so long as they meet the criteria of not causing syneresis, add any anions or ions or compounds that interfere with the crystal structure of the hydrated MMOH and are nontoxic. Also, there were no difficulties making the salve due to the solubility of the thickener.

Any thickeners that were toxic, such as polyethylene glycol high molecular weight related to trace amounts of ethylene oxide or propylene oxide and polyvinyl alcohol, are not in these Tables and are eliminated.

Summary of the Results

Agar, Gelatin, Gellan gum, Konjac, and Tragacanth were eliminated because of their tendency to make non-fluid gels that would prevent the formation of the desirable viscosity of a salve. Several of these candidates were still considered since their property as a dispersant could differ considerably from their property as a gelling agent.

Carboxymethylcellulose (CMC) was eliminated because of likelihood of interaction between carboxylic groups with the MMOH thus reducing its ion exchange property.

Carrageenan was eliminated because of the fact that the commercially available powder contains 15-40% ester-sulfate content which makes it an anionic polysaccharide. Because it is undesirable to utilize any thickener that incorporates anions due to the interaction of anions with the microparticle with their ion exchange capacity, this thickener is deemed unacceptable.

Egg white was considered a doubtful candidate because of variability, but was a positive candidate because of the different chemical protein composition that might result in a singular successful application.

Some of the positive pharmacological properties that were found were as follows:

Chitosan has antimicrobial properties.

Gum arabic has seen a number of positive properties including improved absorption of calcium from the gastrointestinal tract, anti-diabetic, anti-obesity, decreases total cholesterol, kidney and liver support, improved immune function, improvement of the intestinal barrier function.

Hydroxyethyl cellulose improves the dissolution of drugs into the gastrointestinal fluids.

Because the salve is unlikely to be ingested, except in small amounts from an animal licking the site of application of the salve, none of these properties is considered to be of any major importance.

All of the other thickeners were evaluated for their dispersant and suspension properties. In almost all cases, they failed because of their inability to stop syneresis or in some cases their ability to exacerbate the problem.

The cellulosic thickeners performed the best in all cases with the additional requirement that only high molecular weight polymers be considered. Methyl cellulose (MC) and hydroxypropyl methyl cellulose (HPMC) were considered the best.

For further measurements of these acceptable thickeners the following amounts and ratios of the formulation components have been derived. Hydrated MMOH 2/3:Cellulosic thickener 1/3, including the water. Salve: hydrated MMOH 50-80% wt.; Cellulosic thickener 0.5-2.5% wt.; and 15-35% wt. additional water.

Prior to this invention, it was unknown which thickeners would permit the salve to form and which of these selected thickeners to add to the MMOH crystals to form the present salve or lotion. There is no antimicrobial agent or anti-itch agent needed or added to the present formulation. Selection of the thickener is important as it must meet the stated criteria and most thickeners will not be effective in the present formulation. To even begin to select the thickener to use with MMOH crystals, one must understand the nature of these MMOH crystals. There is very little research being done in this inorganic area with MMOH for the last 30 years since the publication of the patents by Burba. These inorganic crystal structures must not be disrupted with the thickener selected while still enhancing the viscosity of the salve and being able to form a adduct while retaining the desired properties of the present formulation.

Only a very few thickening agents are usable, and only at certain concentrations and within a narrow pH range of from 6.5-8.

It is important what thickener is selected to attain this desired viscosity result. The thickeners must not have anions present because the anions would be picked up by the microcrystals and not only destroy some of its antimicrobial property but also tend to promote phase separation. Additionally, the molecular composition of the thickener must not have the wrong charge distribution in its molecule because that too will promote phase separation. Also, for these claimed methods of use these thickeners must not be toxic. Very few inorganic microcrystal compositions are known that are nontoxic as their intended uses are usually for non-pharmaceutical applications. Limited research has been done using only inorganic compounds and components to make a pharmaceutical.

The present salve of the formulation has:

A ratio of 2/3 by wt. of hydrated MMOH mixed with 1/3 by wt. viscous, aqueous thickener solution.

The hydrated MMOH contains >90% water.

The aqueous thickener contains from about 0.5 to about 5% wt. of dry thickener, with the thickener preferably a Cellulosic thickener. Water in an amount 15-35% wt. must be added to make a highly viscous slurry. This water can be added as a one pot mixing process or in advance as described in this application.

The percent solids in the salve is about 5 to about 8% by wt.

The percent hydrated MMOH in the salve is from about 50 to about 80% by wt., preferably from about 63 to about 71% by wt.

The percent water in the salve is from about 85 to about 97% wt., preferably about 90 to about 95% wt. when the water present in the MMOH is included as total water.

The preferred thickeners are cellulosic thickeners having alkyl groups selected from methyl, ethyl, a mixture of methyl and ethyl, hydroxypropyl, and hydroxyethyl. The maximum molecular weights are 1,200,000 for HPMC, 1,300,000 for HEC, 200,000 for HPC, and 220,000 for MC. The amount of thickener present in the salve is from about 0.5 to about 5% wt.

The pH is about 6-9 and reduces stinging on being applied.

Optional Additives

Some constituents must be studiously avoided in the present formulation of the salve or lotion. Surfactants almost always destroy the crystallinity of the MMOH. Some anions tend to occupy the cationic sites on the crystals and destroy the antimicrobial property. A pH below about 6 either destroys the crystals or adversely affects the antimicrobial property. Even vigorous mixing shear can destroy some or all of the crystals and change the properties of the MMOH. After considerable testing, very few additives can be added that do not adversely impact the present formulation.

What was not understood by Burba in trying to make a salve (U.S. Pat. No. 5,154,932), was the fact that when a thickener is added (as tried by Burba with bentonite) to the hydrated microcrystals formed in a filter cake, they are dispersed; but in that process the microcrystals give up some of their waters of hydration, which reduces the overall viscosity of the slurry rather than increasing the viscosity as anticipated. This result goes against conventional thinking. Consequently, much more thickener must be added than anticipated to obtain a stable dispersion. It is also important what thickener is selected to attain this this result. The thickeners must not have anions presents because they are picked up by the microcrystals and not only destroy some of its antimicrobial property but also tend to promote phase separation. Additionally, the molecular composition of the thickener must not have the wrong charge distribution in the molecule because that too will promote phase separation. Also, for these present methods these thickeners must not be toxic.

However, Burba's patent(s) does not mention the problem of "relaxation" of the filter cake creating separation into two phases and the related difficulty of making a product in which this separation does not occur and is in fact avoided. It also does not mention the problems of mixing the crystals with various thickeners, which often cause agglomeration or other undesirable changes, nor does it mention the peculiar attributes of the thickened products. To attain the present formulation all of these issues needed to be solved. Burba failed to address or understand how to avoid or minimize any of these issues.

Preparation of the Present Formulation

The hydrated MMOH of Formula (I) is changed into a liquid salve by moderate shear mixing with water containing a nonionic thickener as discussed above. The resulting slurry holds the microcrystals in the stable suspension required for an acceptable salve or lotion. The aqueous phase, consisting of either a dilute sodium chloride solution or a dilute ammonium chloride solution is discarded.

Formulation of MMOH

It has been found that it is difficult to stably suspend these MMOH crystals in a salve or lotion for several reasons. First of all, the MMOH crystals interact in such a way that they form a solid filter cake which gradually relaxes into a liquid state and separates into two phases, one of which is primarily water. This property is carried over to the formation of a salve or lotion such that a propensity to separate into two phases occurs. This phase separation is quite unsatisfactory for a useful product, e.g., appearance in the container to the consumer, dose distribution in use of the product, and shelf life.

The formulation using these MMOH compounds to provide antimicrobial products can be achieved in the following general way. Compositions containing insoluble particles are separated from the initial reaction mixture (e.g. by filtering, centrifuging, or decanting). The material is dispersed in aqueous or partially aqueous media, washed to remove any residual base, then a thickener is added, either pre-dissolved or dry, optionally adding when needed a Lewis acid to adjust the pH to near pH 7, and mixing/or shearing is continued until a smooth, thickened aqueous system is obtained. A thickener that is hot water dispersible requires a water temperature of at least 190° F. but it does not go into a solution and thicken until it is cooled.

Additionally, the positively charged particles are very prone to interact with the thickening agent in such a way as to either create a material of "putty like" or "apple sauce like" consistency, neither of which are desirable pharmaceutical or marketable properties. Furthermore, the positively charged particles are prone to interact with the thickening agent in such a way as to dramatically change, disintegrate or destroy the ability of said formulation to suspend the particles. Sometimes the thickening agent reacts with the particles in such a way as to destroy the crystalline structure of the particles and their inherent positive charges.

It is therefore important to select the MMOH particles and the thickener used to prepare the present salve or lotion to achieve the desired results without incurring these other issues.

The formulated compositions preferably are salves, lotions, and diluted lotions. A separate activator is not needed to catalyze the reaction. Optionally, other known, usual pharmaceutically-acceptable ingredients can be present in the formulation in limited amounts and selected to meet the criteria required of the salve, such as excipients, suspension aids, preservatives, buffers for pH adjustment, and others which are well known to one skilled in this art. A therapeutically-effective dose of the insoluble particles is administered as a pharmaceutically-acceptable salve, lotion or diluted lotion into or near the diseased cells or cells needing treatment.

The various methods used to make the present salves and lotions are provided below.

Salve Preparation

Method A.

One general method for making a salve of this invention has two solutions prepared. One solution is about 15 L of an aqueous mixture of the desired MMOH. The other solution is 15 L of aqueous 1.13M NaOH. The two solutions are reacted by use of a reaction tee where one solution is in each arm of the tee. The flow rates through the tee were sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of 0.82.

A crystal suspension agent of high molecular weight, hot water dispersible HPMC is prepared in the following manner. 3 L of water are heated to a boil. To this stirred hot water 133 g of a high molecular weight HPMC powder was gradually added. When the HPMC is well dispersed in the stirred hot water, 3 L of cool water is slowly added. A very viscous solution resulted weighing 6.13 Kg.

This viscous solution is mixed into the above MMOH gel in a weight ratio of 1.25 Kg of the viscous solution to 2.5 Kg of MMOH gel. The mixing is done utilizing a vortex paint mixer which gives a moderately high shear rate without destroying the MMOH crystals. The resulting product was a salve. This salve is not prone to separate into two phases, has a smooth homogenous texture, dries to a transparent glossy film and exhibits good antimicrobial properties as shown in Examples I, III and IV.

This method is discussed in detail in Example 1 below. This method has advantages in the ease of preparation, speed of formation of the MMOH with relatively few steps to make the salve.

Method B.

Heat 3.20 Kg of distilled water to 97° C., pour it into a change can or double arm mixer vessel and gradually add 145 g of HPMC powder. Mix gently until a homogenous slurry of the powder and the hot water is produced. Gradually add to the mixer vessel 3.2 Kg of 2° C. distilled water. Mix until a homogenous viscous solution is achieved. To this viscous solution, while running the mixer at a slow speed, slowly add 12.8 Kg of MMOH as prepared in the first paragraph of Method A. Mix until a homogenous salve is produced.

Method C.

Place 12.8 Kg of MMOH at 2° C. into the change can or double arm mixer vessel and add 3.2 Kg of distilled water at 2° C. Mix slowly until a homogenous slurry is achieved. Heat 3.2 Kg of water to 97° C. and put it into the bowl of a second running mixer, then slowly add 145 g of high molecular weight HPMC powder into the bowl. Mix until a homogenous slurry is achieved. Slowly add the hot slurry to the vessel of the running change can or double arm mixer containing the cold MMOH slurry. Run the change can or double arm mixer until a homogenous salve is achieved.

Any of these methods A through C can be used to make the formulated MMOH salve by selection of the desired metals, especially useful are Mg and Al Lotion Preparation In general, a lotion is more liquid (has a lower viscosity) than a salve. Because the MMOH still requires thickening without have phase separation occur in the final lotion, it is somewhat harder to control the process.

One such process is to the vessel of a running change can or double arm mixer add 1.2 Kg of RT deionized water. Slowly add 100 g of a low molecular weight, cold water dispersible Methocel® (trademark of The Dow Chemical Company), i.e., methylated cellulose, including methylcellulose and mixed cellulose ethers having methyl groups, as a powder to the mixer. Mixing is continued until a homogenous liquid gel is achieved. To this gel in the running mixer, slowly add 2.5 Kg of MMOH filter cake as prepared in Example 1. Mix until a homogenous lotion is produced.

Salve Properties

The present salve has excellent hand properties and is easily applied as a smooth coating, which dries to a transparent film with a glossy finish. The salve is very astringent. As water evaporates from the salve surface, the salve tries to replace it with water from the surface underneath. As the waters of hydration evaporate, the concentration of the microcrystals in the film increases and this presents an ever increasing positive charge to the underlying surface. Since the antimicrobial effect is related to the positive charge, the film becomes more antimicrobial as it dries. This is a very desirable property of the present salve.

Methods of Use of the Formulation

The MMOH are positively charged particles held in a stable aqueous suspension utilizing certain thickeners. The present formulation when applied, made by the application protocol as described in this application, has many properties.

(1) It is very resistant to syneresis and phase separation. This property allows for uniform dosing in the salve or lotion which is important to the treatment application. Also, when it does not separate, it increases the shelf life of the product. Additionally, when it separates, customers tend to think is has "gone bad".

(2) It has excellent hand properties (i.e., meaning how the formulation feels when applied) and is easily applied as a smooth coating which dries to a glossy transparent film.

(3) The salve is very astringent. As the applied salve dries, the outermost waters of hydration are lost first to evaporation, but the salve then has a strong attraction for replacement of these water molecules which it acquires from the skin or surface to which it was applied. As these waters of hydration evaporate, the concentration of the microcrystals in the film increases and this presents an ever increasing positive charge to the underlying surface. Since the antimicrobial effect is related to the positive charge of the MMOH microcrystals, the film becomes more antimicrobial as it dries. This occurs without any added antibacterial agent present in the present salve.

This astringent nature of the MMOH salve or lotion is quite useful for certain applications. The salve can dry a weeping lesion and make it heal more rapidly. The film that forms makes it effective for treatment of open wounds where it is desirable to absorb blood serum and stop bleeding or the exudation of blood serum. Additionally, the astringent nature removes some blood serum through the thin burn damaged epidermal membrane, thus preventing the formation of blisters. Furthermore, the astringent nature of the salve and the high concentration of aluminum (Al) and magnesium (Mg) metal ions may, through the process of diffusion, enhance the effect of extracting blood serum through the damaged epidermis at the site of the burn and preventing the burn from developing a blister.

(4) Furthermore, since the anion exchange capacity of the microcrystals is presented in ever increasing concentration, the film acquires more and more affinity for some allergens, an attribute for treating allergic contact dermatitis and sequestering certain contact allergens and attract the venom of certain insect and marine organisms. The antimicrobial property of the MMOH particles trapped in the nontoxic and non-systemic film resulting from the dried in place application of the present formulation, kills negatively charged pathogens, including most bacteria, viral, yeast, and fungal cells on a wound, while also forming a film that protects the wound from further infection. This film enables the wound to frequently not require further dressings or bandages, which is beneficial on animals where retaining the dressing may prove difficult. dressing for wounds or lesions, thereby eliminating the need for bandages. In some cases, this film is greatly superior to conventional wound dressings because it promotes better regeneration of skin over an open wound from the damaged edge of the skin without the formation of scar tissue.

(5) The applied formulation forms a film that shrinks as it dries, thereby reducing stress on nerves in the skin and causing a palliative analgesic effect, perhaps due to reduced tension on the nerves in the skin. These positively charged MMOH particles of the present formulation are repelled from most body tissue and therefore cause little undesirable tissue damage. The entrapped MMOH particles form a positively charged film which reduces the incursion of blood cells and serum to a wound or burn site which speeds healing.

(6) Also, the many waters of hydration of the MMOH in the present formulation give the applied salve or lotion a desirable cooling and analgesic effect on fevered or thermally burned skin tissue. This too, may be attributed to the many waters of hydration and their evaporation. This is particularly useful for soothing fevered or burned skin tissue.

(7) The nontoxic property of all components makes the present treatment desirable for lesions and wounds in the mouth. Similarly, these properties of the present formulation make the treatment optimal for wounds, rashes, contact dermatitis and lesions on children and animals where there is the possibility of ingestion. The non-systemic property of the MMOH particles makes a dilution of the lotion a candidate for treatment of infections of the urinary tract, the large intestine, the vagina and the uterus.

Because the formulations of the present invention comprise three components: MMOH, a specific non-anionic thickener and water. The selection of each of these components is important to achieve the desired results for the salve or lotion and its various uses. Each of these components have been discussed above. No other additives are needed to have the salve function for the various intended uses. In any treatment where the various properties of the salve are suitable for such use, the present formulation may be used. These properties of the salve or lotion therefore provide many suitable uses in treating multiple pharmacological objectives. The common requirement is the use of the present salve or lotion for such treatment. The present formulation is unusual as it provides all these advantages without entering the blood stream as is the case with many pharmaceuticals for such treatments. (see Example XXIII)

While not wishing to be bound by theory, the mechanism by which the present MMOH formulations deactivate the bacteria, germs, microbes and other pathogenic microorganisms is probably best explained as one in which the positive charged crystals of MMOH interact with the negative surface charges that are present on the membrane surfaces of the microorganisms, coating the surface and effectively limiting or preventing the reproduction of the organism by killing it or otherwise inhibiting it.

The infection mechanism resulting from the charge of the microbe depends on the ability of the microbe to attach itself to the positively charged cell being infected. Most cells making up the body have a positive electrical charge, thus requiring pathogens to have a negative electrical charge in order to make the attachment. Part of the efficacy of the microbe requires that it pass on its changes to the RNA and DNA of the body tissue of the cell and depends on the pathogen's ability to attach itself to the cell being infected. If the pathogen mutates to a form that has a different surface charge, it would lose its ability to infect cells. Therefore, the present MMOH formulation is uniquely capable of not causing the pathogen to mutate to a form that is resistant to this MMOH formulation.

This present formulation can treat many conditions that require these properties. Some possible uses are: bacterial, viral, and fungal infections, including those that are caused by pathogens that have developed antibiotic resistance; insect bites of many types as the present formulation sequesters such poisons as the formic acid which constitutes most ant poison and other insects; other "bites" such as spider bites, mosquito bites, chiggers bites, stinging hairs such as those found on asps and spiders; most contact dermatitis conditions where the present formulation sequesters the allergen; burns, including greatly reducing, at least in part, the tendency of burns to the skin to create blisters (thought to be by an apparently complex mechanism which involves the response of certain blood cells that recognize the positive charge of the MMOH film lying on the damaged epidermis); bruises or subcutaneous hematomas (using the same mechanism which tends to keep burns from blistering).

When the filter cake was first made, it was tested for its antimicrobial properties using in vitro tests utilizing multiple pathogens. The efficacy as an antimicrobial is derived from the positive charge on the microcrystals. This positive charge also determines the anion exchange capacity of the aqueous slurry. Thus, for the purposes of this application, the antimicrobial property was quickly determined by measuring the anion exchange capacity of the salve at a given set of conditions. All the compounds of Formula (I) are expected to display these properties based of the testing of a variety of these combinations within Formula (I).

Surprisingly, potential applications of this property of treating antibiotic resistant pathogens are suggested for several internal applications as well as the surface applications. Because these present microcrystals have demonstrated the inability to penetrate body tissue and enter the blood stream, this antimicrobial property would be invaluable for treating pathogens in the various cavities, such as an oral cavity (mouth), large intestine, the urinary tract, and the female reproductive tract where the area of treatment would be localized and not harmful in the blood stream. In each of those areas, there are many cases of infections caused by pathogens which are resistant to treatment with known antibiotics. This inability to enter the blood stream is shown in Example XXIII In the following examples, the variety of uses are provided as illustrations of the many possible uses of the present formulations, but are not to be construed as inclusive of all possible uses of the present formulation.

The present formulation provides a salve or lotion that is not subject to syneresis and provides astringent properties. To attain these results, all three components of the formulation must be present in the amounts and ratios given in the claims and taught in this application. None of these components alone can provide these results, including those listed above. Thus, the selection of the desired MMOH (a subset of the MMOH taught by Burba) using nontoxic metals is needed, the thickener must be carefully selected to interact with the MMOH but without disturbing the positive charge or the crystalline layers and nature of those crystals, and sufficient water must be used to provide the needed viscosity of the salve or lotion while still allowing for the waters of hydration present in the crystals. If any of these components is not carefully selected, the results desired for the salve or lotion is not attained. Clearly, it has been found that the specific combination of these three components is required for the formulation to provide the treatments desired. To show these components and the various selections, the following comparisons are provided.

Comparison Discussion

Because some prior art has made some these MMOH compounds of Formula (I), the present invention has found that only certain ones of these MMOH compounds are possible for the present invention. The present uses require that the formulation, including the components, be nontoxic. Burba had no such requirement for the uses in oil well drilling fluids, his main use. The present MMOH component is a subset from that of Burba both for the metals used and the scope of the MMOH possible. Thus, the metals used and amounts are important in these pharmaceutical formulations. Burba did not teach such a subset of MMOH crystals.

Some of the reasons why this present formulation was never made, although some attempts have been tried, involves the properties of the MMOH crystals. As discussed above for these MMOH crystals, the phase separation which happens was a difficult problem to overcome and not well understood. To solve this problem required going against conventional thinking.

MMOH is a known thickener and The Dow Chemical Company tried to sell it as such. However, the more MMOH crystals that were added to the thickener initially lower the viscosity of the slurry. This was the reverse of what was expected. It was not understood why the MMOH crystals alone would not make a salve of the desired viscosity.

It has now been found to make the present salve from the MMOH crystals requires the addition of other specific thickeners in rather large amounts. This has been discussed above as to the present thickeners needed. However, the idea of having a thickener to which you must add appreciable amounts of a second thickener in order to have it make a salve is counterintuitive to all conventional concepts. In fact, when Burba tried to do so using bentonite he failed.

For example, when a second thickener is added (as tried using bentonite clay by Burba in cited patents above) to the hydrated microcrystals formed in a filter cake, they are dispersed; but in that process, the microcrystals give up some of their waters of hydration, which reduces the overall viscosity of the slurry rather than increasing the viscosity as anticipated. Consequently, significantly more thickener must be added than anticipated to obtain a stable dispersion. In fact, more thickener is required because it is believed that the MMOH microcrystals are diluting the slurry even more than expected. The present amounts as claimed are needed to be successful to form a salve of this present invention. The amount of dry thickener powder that must be added is from about 0.5 to about 3% wt. depending on the number of waters of hydration present in the MMOH and the specific thickener selected. This realization of the amount and the selection of the appropriate thickener was never understood or envisioned prior to this invention.

Burba Comparison

While not wishing to be bound by theory, it is believed that when the MMOH microcrystals are dispersed as an aqueous slurry, they give up some of their multiple waters of hydration. This added water then dilutes the thickener and the viscosity goes down. Unless the present invention is used with the three components in the amounts indicated, the MMOH crystals will display syneresis and form agglomerates in the salve and cause phase separation. When additives are present, like the bentonite clay that Burba used to try to prevent this issue, then the surface charge of the MMOH is affected by the additive, which significantly reduces the effectiveness of the MMOH attempted salve. The MMOH forms an adduct with the thickener such that the interaction often adversely effects the formulation by altering the charge of the MMOH component and the adduct.

Figure 2:
FIG. 2 has three vials as A2-C2 that are photographs taken on Apr. 14, 2022 of salves made by the procedure of Burba and the present invention. FIG. A1 is the present invention, Example 10; FIG. B1 is Burba's MMOH with water addition, Comparative Example A; FIG. C1 is Burba's MMOH with bentonite addition, Comparative Example B.
Figure 3:
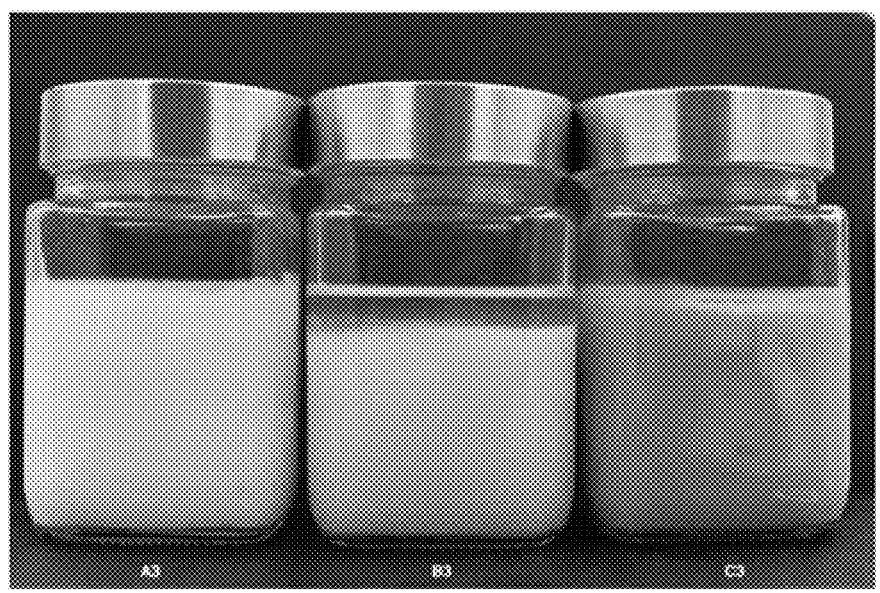
FIG. 3 has three vials as A3-C3 that are photographs taken on Jul. 17, 2022 of salves made by the procedure of Burba and the present invention. FIG. A1 is the present invention, Example 10; FIG. B1 is Burba's MMOH with water addition, Comparative Example A; FIG. C1 is Burba's MMOH with bentonite addition, Comparative Example B.

A major problem of making a salve that is marketable results from the MMOH crystals is their property of syneresis. This was shown by Burba's attempted salve's issues in 1990 which resulted in phase separation. How to solve this problem was not successful by Burba's methods. To better explain this problem, it was necessary to produce salves with Burba's procedures (Comparative Examples A and B) and then compare his presumed salves with salves made by the procedure used by the present invention (Example 10). These salves were prepared by aging both the Burba samples and the instant application sample for the same lengths of time to evaluate phase separation. FIGS. 1-3 show the comparative results of these samples after intervals of one month, three months, and seven months after manufacture. The instant application salve's results are labeled FIG. A; Burba's attempted salve's results are labeled FIG. B for his water addition preparation, and FIG. C for his bentonite addition.

Furthermore, the Burba's film differs from the one produced using the HPMC crystal thickener in Example 10 principally in that it gives a gritty hand feel and a much rougher and less glossy finish film with lower durability.

Although Burba tried to make a salve, he just sent the MMOH dispersion, made similar to Comparative Example A, to Merrill, Dow's pharmaceutical subsidiary at that time, for evaluation for its useful properties he had envisioned; they rejected it as a salve.

Burba knew from his research into the application for drilling fluid that the MMOH adduct formed with bentonite did not separate as badly as MMOH in water, so he tried to make a salve. Burba tried to use bentonite clay as a thickener as shown in Comparative Example B. The attempted salve went on smoothly, but dried into a transparent film with an undesired rough unpleasant hand feel. Even so, the greatest weakness of the attempted salve was uncovered by the quality control test which revealed a much weaker positive surface charge presented to the underlying skin or body tissue. The presence of the bentonite particles must therefore interfere with the crystals in closest proximity to the skin or body tissue, and thereby the positive charge of the MMOH crystals is diminished and the antimicrobial properties of the attempted salve are greatly reduced. A sample of this attempted salve was placed in a transparent container which was compared to the salve prepared from the present protocol for a period of three months. Photographs were taken and saved for comparison. Photographs of Burba's attempted salve with bentonite prepared by this protocol are labeled FIGS. C1, C2 and C3.

In the following examples, the variety of uses are provided as illustrations of the many possible uses of the present formulations, but are not to be construed as inclusive of all possible uses of the present formulation.

This invention will be further clarified by a consideration of the following examples, which are intended to be purely exemplary of the present invention. The numbered examples are illustrative of this invention's formulated MMOH; the Roman numbered examples show use of the present invention's formulation and effectiveness; and the lettered examples are comparative examples.

EXAMPLES

Example 1: Salve of MMOH of Mg and Al Hydroxides Using Hot Water Dispersible HPMC Two solutions were prepared, one solution was 15 L of an aqueous mixture of $MgCl_2$ and $AlCl_3$ (0.21M Mg and 0.23M Al). The other solution was 15 L of aqueous 1.13M NaOH. The two solutions were reacted by use of a reaction tee where one solution is in each arm of the tee. The flow rates through the tee were sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Mg/Al of 0.82.

A crystal suspension agent of high molecular weight, hot water dispersible HPMC was prepared in the following manner. 3 L of water are heated to a boil. To this stirred hot water 133 g of a high molecular weight HPMC powder was gradually added. When the HPMC was well dispersed in the stirred hot water, 3 L of cool water was slowly added. A very viscous solution resulted weighing 6.13 Kg.

This viscous solution was mixed into the above MMOH gel in a weight ratio of 1.25 Kg of the viscous solution to 2.5 Kg of MMOH gel. The mixing was done utilizing a vortex paint mixer which gave a moderately high shear rate without destroying the MMOH crystals. The resulting product was a salve. This salve is not prone to separate into two phases, has a smooth homogenous texture, dries to a transparent glossy film and exhibits good antimicrobial properties as shown in Examples I, III and IV.

Example 2: Salve of MMOH of Mg and Al Hydroxides Using Cool Water Dispersible HPMC Two solutions were prepared, one solution was 15 L of an aqueous mixture of $MgCl_2$ and $AlCl_3$ (0.21M Mg and 0.23M Al). The other solution was 15 L of an aqueous 1.2M NaOH. The two solutions were reacted in a reaction tee, similar to Example 1, at flow rates sufficient to maintain turbulent flow in the tee and to maintain proper stoichiometry. This reaction produced a MMOH product where y is about 0.3, which has a pH of about 7.8. The product was filtered and washed with water to remove byproduct salts and ant excess reagent base. The product remaining on the filter surface was an aqueous gel, which is analyzed and found to be 7.5% MMOH having a molar ratio of Mg/Al of 0.82.

A crystal suspension agent of high molecular weight cool water dispersible HPMC was prepared in the following manner. 6 L of RT water were put into an open topped mixing vessel equipped with a vertical shaft mixing impellor agitating the water so as to create a vortex in the middle. 133 g of high molecular weight cool water dispersible HPMC powder was fed slowly into the vortex. A very viscous solution resulted weighing 6.13 Kg. This solution was mixed into the above MMOH gel utilizing a vortex paint mixer which gave a moderately high shear rate without destroying the MMOH crystals.

This procedure produces a salve. The salve is not prone to separate into two phases, has a smooth homogenous texture, dries to a transparent glossy film.

Example 3: Salve of MMOH of Mg and Al Hydroxides Using Egg White

Two solutions were prepared, one solution was 15 L of an aqueous mixture of $MgCl_2$ and $AlCl_3$ (0.21 MMg and 0.23M Al). The other solution was 15 L of an aqueous 1.2M NaOH. The two solutions were reacted in a reaction tee, similar to Example 1, at flow rates sufficient to maintain turbulent flow in the tee and to maintain proper stoichiometry. The reaction produced a MMOH product where y is about 0.3, which has a pH of about 7.8. The product was filtered and washed with water to remove byproduct salts and excess reagent base. The product remaining on the filter surface was an aqueous gel, which was analyzed and found to be 7.5% MMOH having a molar ratio of Mg/Al of 0.82.

A crystal suspension agent of egg white powder was prepared in the following manner. 1.25 Kg of dried pasteurized egg white powder was added to 4.75 Kg of RT water and mixed in a high shear mixer. This process made 6 Kg of a viscous solution which was mixed into the above MMOH gel utilizing a vortex paint mixer, which gave a moderately high shear rate without destroying the MMOH crystals.

This procedure produces a salve. This salve is not prone to separate into two phases, has a smooth homogenous texture, dries to a transparent glossy film.

Example 4: Salve of MMOH of Mg and Al Hydroxides Using Cool Water Dispersible HPMC Two solutions were prepared, one solution was 15 L of an aqueous mixture of $MgCl_2$ and $AlCl_3$ (0.21M Mg and 0.23M Al). The other solution was 15 L of an aqueous 1.2M $NH_4OH$. The two solutions were reacted in a reaction tee, similar to Example 1, at flow rates sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Mg/Al of 0.82.

A crystal suspension agent of high molecular weight, cool water dispersible HPMC is prepared in the following manner. 6 L of RT water was put into an open topped mixing vessel equipped with a vertical shaft mixing impellor agitating the water to create a vortex in the middle. 133 g of high molecular weight cool water dispersible HPMC powder was fed slowly into the vortex. A very viscous solution resulted weighing 6.13 Kg. This solution was mixed into the MMOH gel utilizing a vortex paint mixer which gave a moderately high shear rate without destroying the MMOH crystals, This procedure produced a salve. The salve is not prone to separate into two phases, has a smooth homogenous texture, dries to a transparent glossy film and exhibits good antimicrobial properties as shown in Examples II, land V-XXI.

Example 5: Salve of MMOH of Ca and Al Hydroxides Using HPMC

Two solutions were prepared, one solution was 15 L of an aqueous mixture of $CaCl_2$) and $AlCl_3$ (0.21M Ca and 0.23M Al). The other solution was 15 L of an aqueous 1.13M $NH_4OH$. The two solutions were reacted in a reaction tee, similar to Example 1, at flow rates sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Ca/Al of 0.82.

A crystal suspension agent of high molecular weight cool water dispersible HPMC was prepared in the following manner. 6 L of RT water are put into an open topped mixing vessel equipped with a vertical shaft mixing impellor agitating the water to create a vortex in the middle. 133 g of high molecular weight, cool water dispersible HPMC powder was fed slowly into the vortex. A very viscous solution resulted weighing 6.13 Kg. This viscous solution was mixed into the MMOH gel utilizing a vortex paint mixer, which gave a moderately high shear rate without destroying the MMOH crystals.

This procedure produced a salve which is not prone to separate into two phases, which has a smooth homogenous texture, which dries to a transparent glossy film.

Example 6: Salve of MMOH of Zn and Al Hydroxides Using HPMC

Two solutions were prepared, one solution was 15 L of an aqueous mixture of $ZnCl_2$ and $AlCl_3$ (0.21M Zn and 0.23M Al). The other solution was 15 L of aqueous 1.13M NaOH. The two solutions were reacted in a reaction tee, similar to Example 1, at flow rates sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Zn/Al of 0.82.

A crystal suspension agent of high molecular weight, cool water dispersible HPMC was prepared in the following manner. 6 L of RT water were put into an open topped mixing vessel equipped with a vertical shaft mixing impellor agitating the water to create a vortex in the middle. 133 g of high molecular weight, cool water dispersible HPMC powder was fed slowly into the vortex. A very viscous solution resulted weighing 6.13 Kg. This viscous solution was mixed into the MMOH gel utilizing a vortex paint mixer which gave a moderately high shear rate without destroying the MMOH crystals.

This procedure produced a salve which is not prone to separate into two phases, has a smooth homogenous texture, dries to a transparent glossy film.

Example 7: Salve of MMOH of Mn and Al Hydroxides Using HPMC

Two solutions were prepared, one solution was 15 L of an aqueous mixture of $MnCl_2$ and $AlCl_3$ (0.21M Mn and 0.23M Al). The other solution was 15 L of aqueous 1.13M NaOH, The two solutions were reacted in a reaction tee, similar to Example 1, at flow rates sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Mn/Al of 0.82.

A crystal suspension agent of high molecular weight, cool water dispersible HPMC was prepared in the following manner. 6 L of RT water are put into an open topped mixing vessel equipped with a vertical shaft mixing impellor agitating the water to create a vortex in the middle. 133 g of high molecular weight, cool water dispersible HPMC powder was fed slowly into the vortex. A very viscous solution resulted weighing 6.13 Kg. This solution was mixed into the MMOH gel utilizing a vortex paint mixer, which gives a moderately high shear rate without destroying the MMOH crystals.

This procedure produced a salve which is not prone to separate into two phases, has a smooth homogenous texture, dries to a transparent glossy film.

Example 8: Salve of MMOH of Co and Al Hydroxides Using HPMC

Two solutions were prepared, one solution was 15 L of an aqueous mixture of $CoCl_2$ and $AlCl_3$ (0.21M Co and 0.23M Al). The other solution was 15 L of aqueous 1.13M NaOH. The two solutions were reacted in a reaction tee, similar to Example 1, at flow rates sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Co/Al of 0.82.

A crystal suspension agent of high molecular weight, cool water dispersible HPMC was prepared in the following manner. 6 L of RT water were put into an open topped mixing vessel equipped with a vertical shaft mixing impellor agitating the water to create a vortex in the middle. 133 g of high molecular weight, cool water dispersible HPMC powder was fed slowly into the vortex. A very viscous solution resulted weighing 6.13 Kg. This solution was mixed into the MMOH gel utilizing a vortex paint mixer, which gave a moderately high shear rate without destroying the MMOH crystals.

This procedure produced a salve which is not prone to separate into two phases, has a smooth homogenous texture, dries to a transparent glossy film.

Example 9: Salve of MMOH of Ni and Al Hydroxides Using HPMC

Two solutions were prepared, one solution was 15 L of an aqueous mixture of $NiCl_2$ and $AlCl_3$ (0.21M Ni and 0.23M Al). The other solution was 15 L of aqueous 1.13M NaOH. The two solutions were reacted in a reaction tee, similar to Example 1, at flow rates sufficient to maintain turbulent flow in the tee and to maintain proper stoichiometry, which produced a MMOH product where y is about 0.3, which has a pH of about 7.8. The product was filtered and washed with water to remove byproduct salts and any excess reagent base. The product remaining on the filter surface was an aqueous gel, which was analyzed and found to be 7.5% MMOH having a molar ratio of Ni/Al of 0.82.

A crystal suspension agent of high molecular weight, cool water dispersible HPMC was prepared in the following manner. 6 L of RT water are put into an open topped mixing vessel equipped with a vertical shaft mixing impellor agitating the water to create a vortex in the middle. 133 g of high molecular weight, cool water dispersible HPMC powder was fed slowly into the vortex. A very viscous solution resulted weighing 6.13 Kg. This viscous solution was mixed into the MMOH gel utilizing a vortex paint mixer, which gave a moderately high shear rate without destroying the MMOH crystals.

This procedure produced a salve which is not prone to separate into two phases, has a smooth homogenous texture, dries to a transparent glossy film.

Example 10: Salve of MMOH of Mg and Al Hydroxides Using HPMC

15 L of an aqueous solution of 0.23M aluminum chloride and 0.21M magnesium chloride was prepared. 15 L of an aqueous solution of 1.13M aqueous ammonia was prepared. The metal salts solution and the aqueous ammonia solution were simultaneously pumped at equal flow rates through a mixing tee so as to produce a slurry of MMOH crystals. The slurry was then put into a centrifuge where the MMOH crystals were separated from the filtrate, washed with water to remove soluble reagents, and then spun dry to produce a solid filter cake. A 175,000 centipoise solution was made of 0.133 Kg of K100 Hypromellose (HPMC, hydroxypropyl methylcellulose, from The Dow Chemical Company) in 6 L of water. A salve was then made from 2 Kg of filter cake and 1 Kg of the Hypromellose solution mixed in a low shear mixer. The salve was placed into clear sample containers, at various time intervals, to view for phase separation.

Example 11: Example 1 Smeared on a Black Plate

Figure 11A:
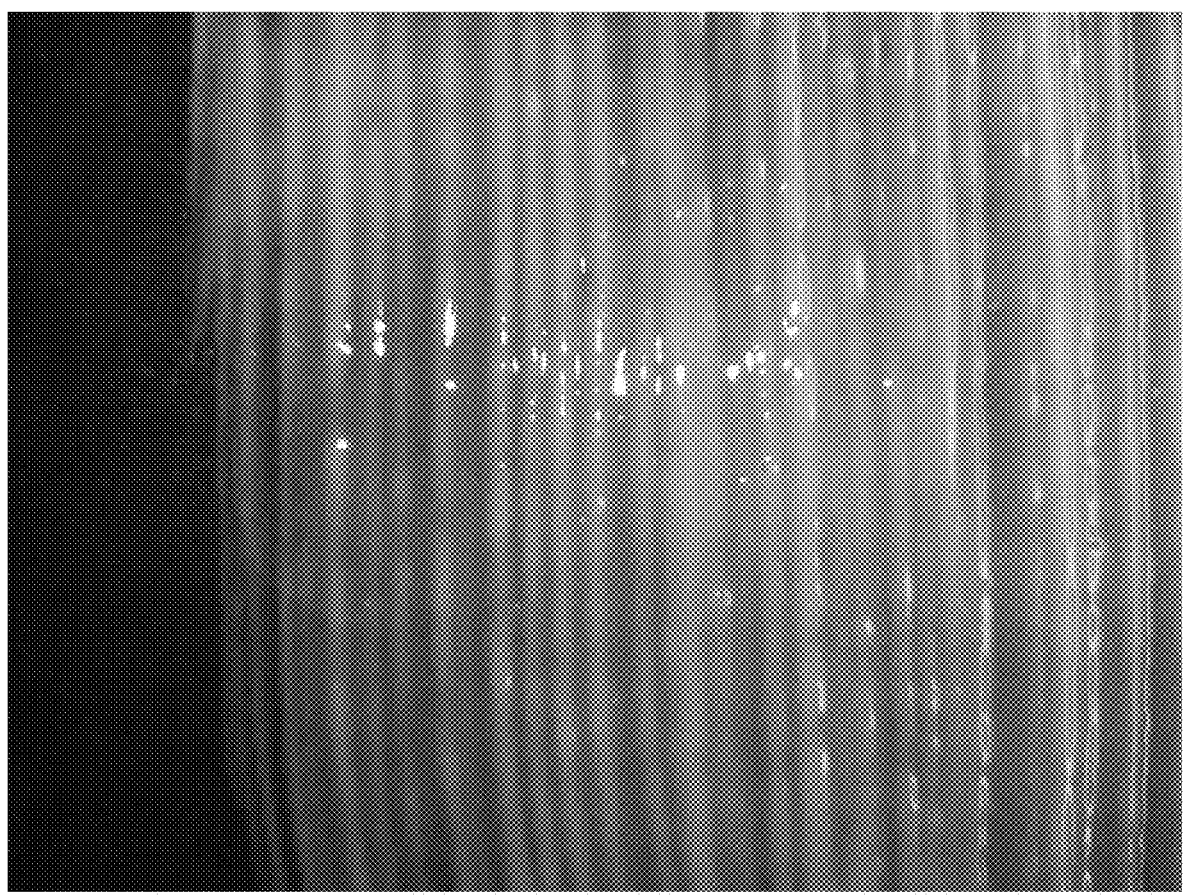
FIG. 11A is a photograph of the salve of Example 1 where 100% is the salve. The MMOH is hydrated. There are no granules visible or formed.
Figure 11B:
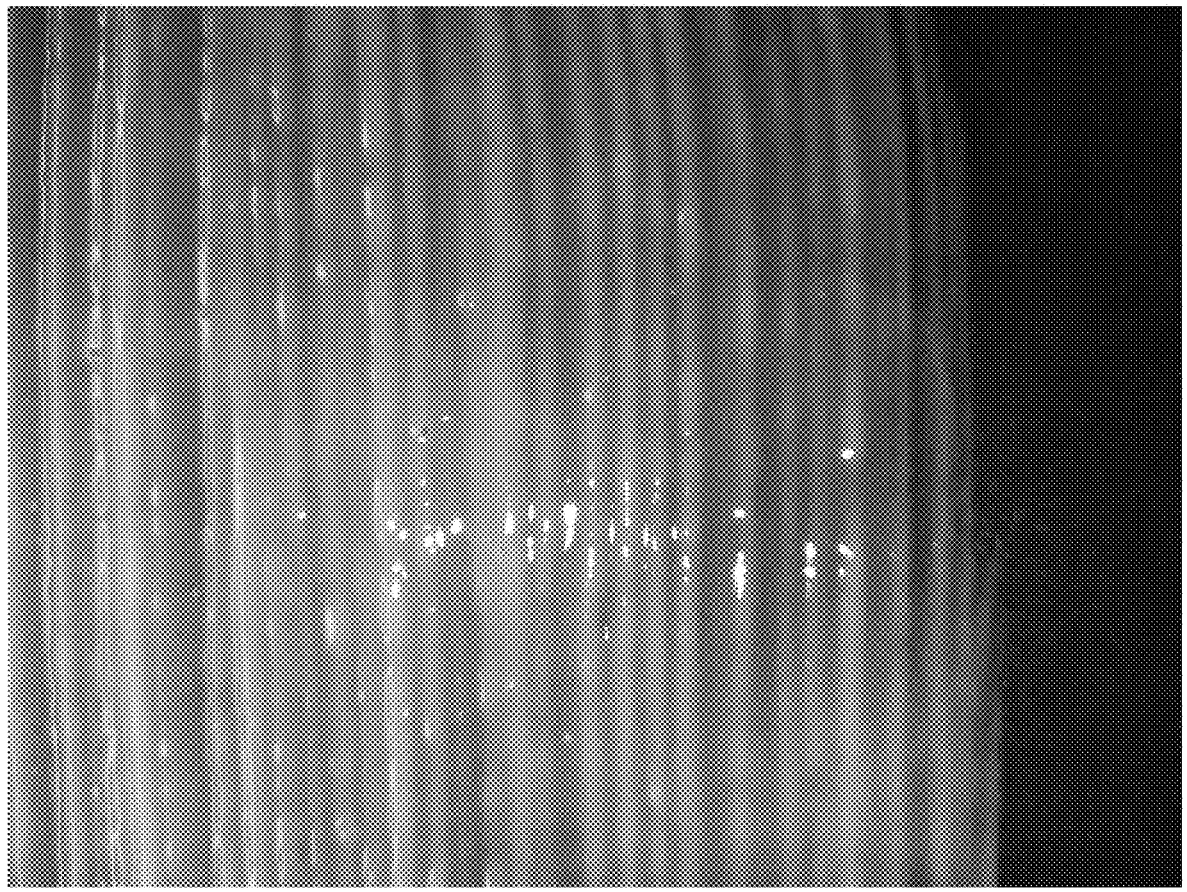
FIG. 11B is of the same salve 14 days later. It is unchanged and has no granules visible or formed.

When the salve of the present invention from Example 1 was smeared onto a black plate, it is apparent from FIG. 11 that uniform mixing occurs throughout the salve as no separation is visible.

Comparative Example A: Presumed Salves Produced by Burba's Method in 1990

15 L of an aqueous solution of 0.23M aluminum chloride and 0.21M magnesium chloride was prepared. 15 L of an aqueous solution of 1.13M aqueous ammonia was prepared. The metal salts solution and the aqueous ammonia solution were simultaneously pumped at equal flow rates through a mixing tee so as to produce a slurry of mixed metal hydroxide (MMOH) crystals. The slurry was then put into a centrifuge where the MMOH crystals were separated from the filtrate, washed with water to remove soluble reagents, and then spun dry to produce a solid filter cake. An attempted salve was then made from 2 Kg of filter cake mixed with 500 g of water by mixing in a low shear mixer. Since no microcrystal suspension or dispersion agent was included in the attempted salve, the crystals start to coalesce and phase separation occurs steadily with elapsed time (see FIG. B1, B2, B3). This is the greatest issue of Burba's attempted salve which lacks a crystal suspension additive.

Comparative Example B: Presumed Salves Produced by Burba's Method in 1990 with Bentonite 15 L of an aqueous solution of 0.23M aluminum chloride and 0.21M magnesium chloride was prepared. 15 L of an aqueous solution of 1.13M aqueous ammonia was prepared. The metal salts solution and the aqueous ammonia solution were simultaneously pumped at equal flow rates through a mixing tee so as to produce a slurry of MMOH crystals. The slurry was then put into a centrifuge where the MMOH crystals were separated from the filtrate, washed with water to remove soluble reagents, and then spun dry to produce a solid filter cake. A bentonite slurry was prepared by vigorously mixing and straining 125 g of bentonite powder with 500 g of water. An attempted salve was then made from 200 g of MMOH filter cake mixed with 80 g of bentonite slurry. The attempted salve thus produced was an opaque gray color but had considerably better resistance to syneresis than the Burba attempted salve produced with no crystal suspension additive in Comparative Example A. A slight amount of phase separation was noted initially, but no more occurred with further passage of time (FIGS. A3, B3, C3).

Comparative Example C: Comparison of Various Commercial Salves where MMOH was Add to them without any Added Thickener General preparation of the mixture.
Adding MMOH into a commercial salve involved taking 5 g of hydrated MMOH in a beaker mixing with 20 g of commercial salve using a stirring rod by hand. The formulations were not miscible on stirring as evidenced when the mixture was smeared on a black plate.

Figure 8:
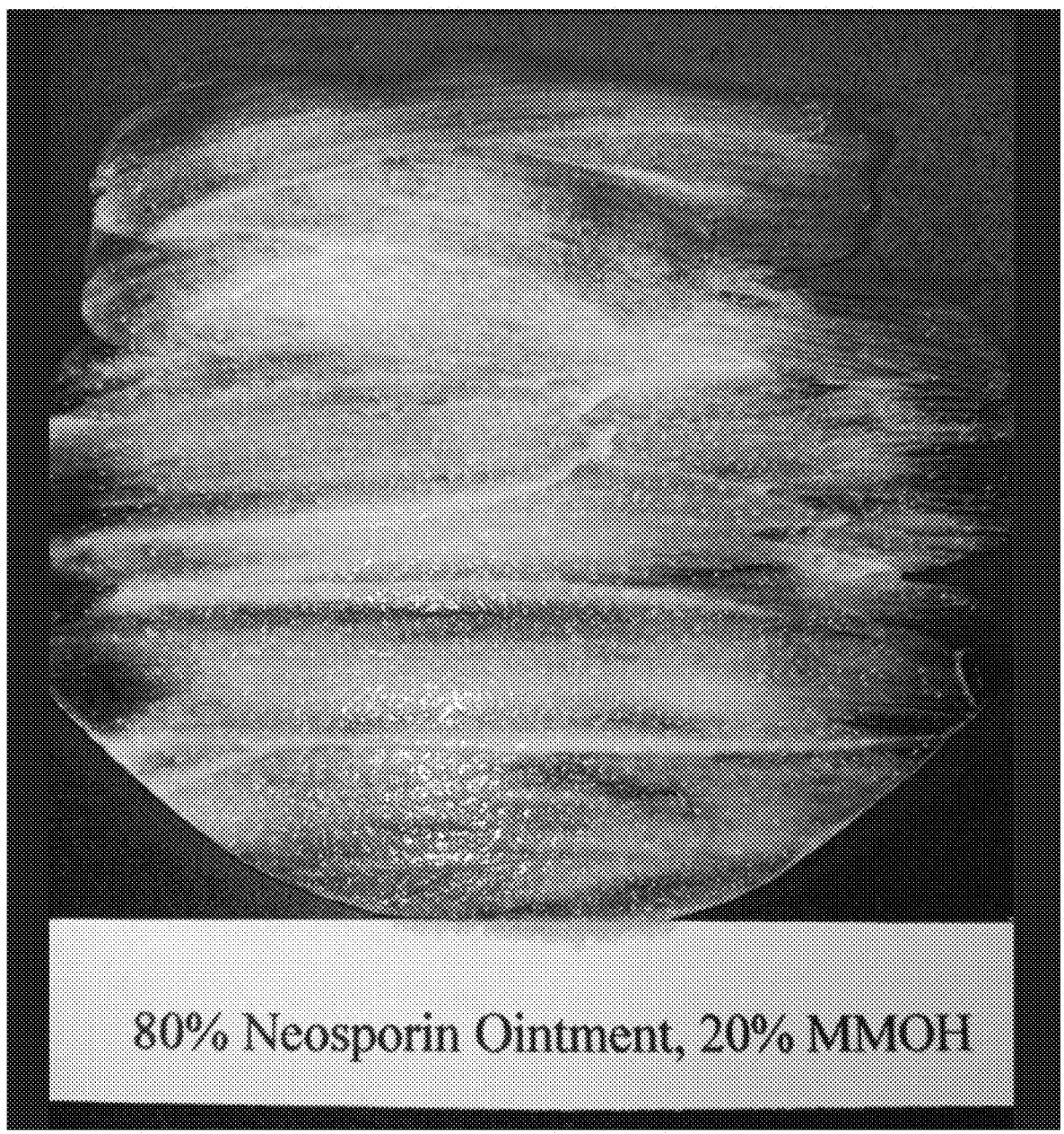
FIG. 8 is a photograph of a mixture of a Neosporin salve where 80% is the Neosporin salve and 20% is Burba's MMOH of Comparative Example A. The dehydrated MMOH in powder form did not dissolve in the salve and appears as granules.

Neosporin. In FIG. 8 purchased Neosporin salve had 20% wt. of MMOH added to 80% wt. of the salve to see if a salve of this present invention could be made. If the fully hydrated MMOH is used, the two materials simply cannot be made into a homogenous mixture. Just like oil and water do not mix. If the dehydrated from of MMOH is used, there is not enough water in the matrix to rehydrate the MMOH to the essential hydrated form. As seen in FIG. 8, the dehydrated form of MMOH in the form of a powder is mixed with the salve. The two formulations were manually mixed in a beaker and the mixture was smeared on a black plate. The photograph was taken ten minutes after application to the plate. The photograph shows that the MMOH particles show no sign of rehydrating and the mixture is nonhomogeneous with poor hand feel and poor properties. Clearly 2 phases are visible. The MMOH would not provide any advantage to the salve and the other ingredients in the Neosporin salve does not disperse the MMOH. The features of claim 1 do not occur with this mixture—no film forming, astringent property and others.

Figure 9:
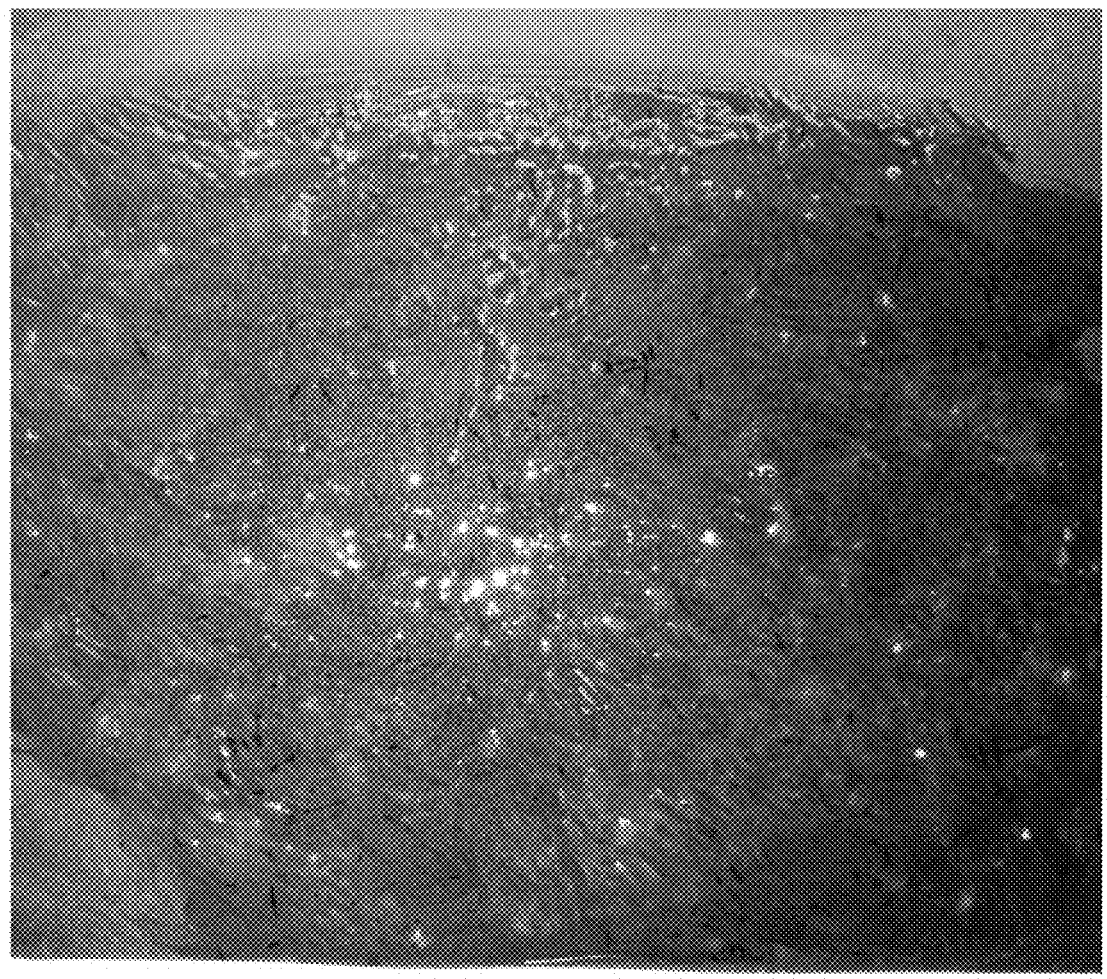
FIG. 9 is a photograph of CVS Antiseptic cleanser where 80% is the cleanser and 20% is the dehydrated form of Burba's MMOH of Comparative Example A. The dehydrated MMOH in powder form did not dissolve in the salve and appears as granules.

CVS Antiseptic cleanser. When the above general process was repeated with this salve, FIG. 9 shows that the mixture looked nonhomogeneous, similar to Neosporin results. MMOH also showed separate phases as granules in the salve and did not form a uniform salve with the properties now claimed.

Figure 10:
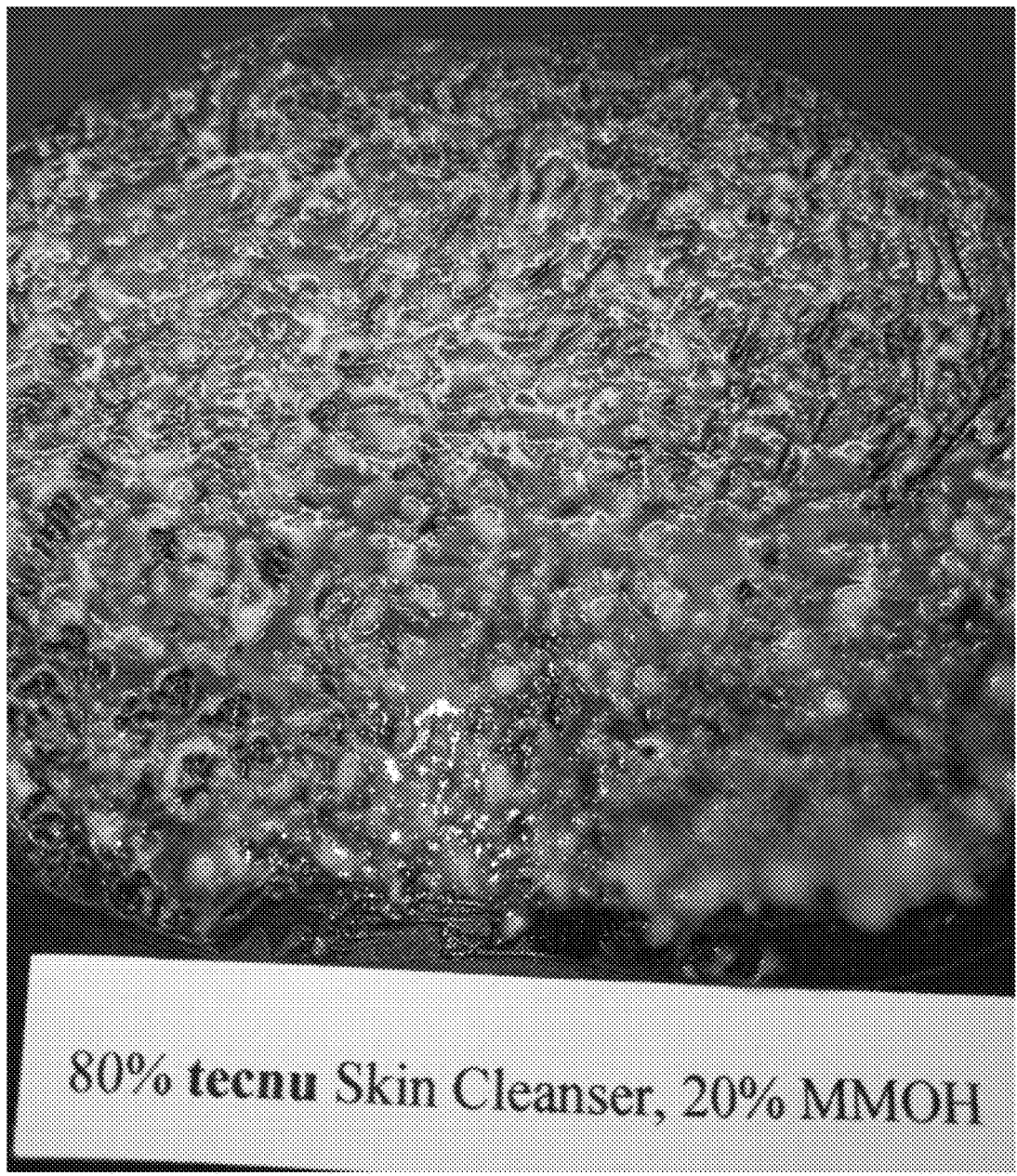
FIG. 10 is a photograph of tcenu cleanser where 80% is the cleanser and 20% is the dehydrated form of Burba's MMOH of Comparative Example A. The dehydrated MMOH in powder form did not dissolve in the salve and appears as granules.

Tecnu cleanser. When the above general process was repeated with this salve, FIG. 10 shows that the mixture looked nonhomogeneous, similar to Neosporin results. MMOH also showed separate phases as granules in the salve and did not form a uniform salve with the properties now claimed. FIG. 10 shows the distinct granules of the MMOH distributed into the salve. They remained as a separate phase and did not produce the properties of the present salve as claimed.

Uses of the Formulation

Example I: Treatment of Herpes Simplex Virus (HSV)

The salve in Example 1 was applied to a cluster of 6 herpes simplex vesicles on the red border of the right upper lip of a 16 year old Caucasian female. The patient complained of irritation and slight pain. Salve was reapplied at intervals of 2 to 10 hours for a period of 5 days. At the end of that period, the vesicles had healed and the pain and irritation were gone.

Example II: Shingles (Herpes Zostra)

A seventy year old Caucasian female had many shingles lesions on the left side of her face, her left eyelid and scalp. The irritation from the lesions were greatly impacting her sleep. She received an ointment from her physician, but it gave little relief. She changed to the salve in Example 4 and applied it to her face and scalp three times daily. It gave excellent relief from pain and allowed her to sleep. Treatment continued for approximately 10 days. At that time the lesions had started to disappear and all discomfort had ceased.

Example III: Seborrheic Keratoses

The salve in Example 1 was applied to two raised light tan roughly circular 0.5 cm Seborrheic Keratoses lesions on the right forearm of an 81 year old Caucasian male. The salve was reapplied daily for 5 days. At the end of that period, treatment was discontinued. On day 8, the lesions sloughed off leaving undamaged skin beneath.

Example IV: Eczema

A roughly 5 cm by 7 cm elliptical lesion of microbial eczema on a 5 year old Caucasian female appeared raw and fissured with scale formation at the periphery. The lesion was treated at intervals of from 1 to 8 hours for 5 days with the salve in Example 1. At the end of that time, all drainage had stopped, redness was gone, and the lesion was healed, except for some temporary remaining crustiness.

Example V: Acne

Two inflamed acne pustules, both about 0.5 cm, were on the face of a 15 year old Caucasian male and showed evidence of having been excoriated. The pustules were treated at intervals of from 2 to 8 hours with the salve in Example 4. After 4 days, all swelling and redness had dissipated. After 6 days, scabs had gone and all signs of the pustules were gone.

Example VI: Impetigo

Six impetigo vesicles or pustules, all about 0.5 cm in diameter were found on the chest of a 10 year old African American male. The lesions were treated at intervals of from 2 to 8 hours with the salve in Example 4. After 7 days, all swelling and redness has gone. After two weeks all signs of the impetigo have gone.

Example VII: Thermal Burn

An 82 year old Caucasian male burned the palm of his left hand severely with the end of a hot air gun. The burn immediately turned bright red and the patient felt a sharp lingering pain. Before it blistered, the burn was treated quickly with the salve in Example 4. The pain immediately subsided, and within 45 minutes, the burn had turned from red to brown. The burn never blistered but a brown circle remained on the patient's hand for a period of 40 days before the top layer of the epidermis peeled off leaving undamaged skin beneath.

Example VIII: Non-Sutured Wound in a Horse

A four year old quarter horse gelding was severely injured from a collision with a barb wire fence during a thunderstorm. The skin was cut halfway around the periphery of the uppermost right leg creating a wound about 30 cm long horizontally and 17 cm vertically. The muscle beneath the skin was injured as well, creating a furrow about 2 cm deep and 10 cm long. The horse was not taken to the veterinarian for about three days, and by the time of its arrival at the veterinarian, the wound was infected with both *staphylococcus* and *E. coli* bacteria. The wound was washed vigorously with water and then painted with the salve in Example 4. This treatment was repeated once daily for a period of 90 days. After three days, all signs of infections were gone, and serum was no longer running down the horse's leg. After 75 days, the serration of the muscle had disappeared. After 90 days, the wound was closed completely without any sign of scar tissue. The salve alone had dressed the wound.

Figure 6A:
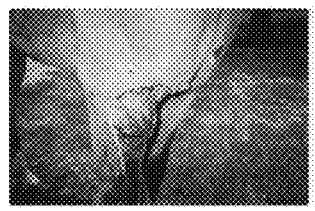
FIG. 6A is the admission time (time I) shown by the veterinarian of the horse with a leg injury with serum running down the leg.
Figure 6B:
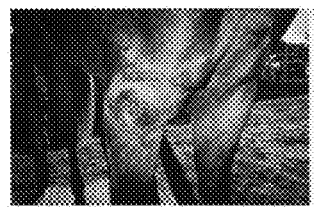
FIG. 6B is 45 days from time I where no serum is present running down the leg and the wound if clean.
Figure 6C:
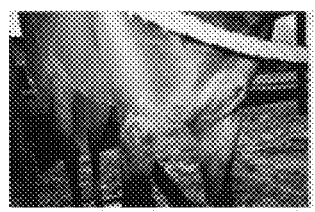
FIG. 6C is 75 days from time I where to wound is still clean and greatly diminished in size.
Figure 6D:
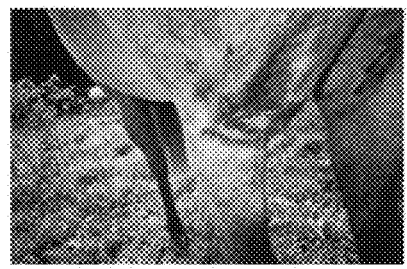
FIG. 6D is 90 days from time I and the wound is completely closed and hair has begun growing in the area. The lighting was not controlled for these pictures such that shades color occurred. The horse fully recovered.

FIG. 6A is the initial intake (time I) of the horse with the injury by the veterinarian. FIG. 6B is 45 days from time I. FIG. 6C is 75 days from time I. FIG. 6D is 90 days from time I. The lighting was not controlled for these pictures.

It was surprising to see such an expanse of exposed muscle without any blood or serum coming from the wound. It was even more surprising to see the wound heal without scar tissue. FIG. 6 shows this time series of treatment. In FIG. 6B the dried salve over the wound is apparent. Signs of infection decreased and no scar happened on healing. The horse fully recovered.

Example IX: Sunburn

An 81 year old Caucasian male was badly sunburned on the forehead, cheeks and neck while on a one day fishing trip. Upon returning home from the trip in the evening, the patient complained of considerable pain and treated all of the sunburned skin with the salve in Example 4. The salve dried and produced a transparent film over the affected skin which was allowed to remain in place. The pain immediately subsided and never returned. The burns never hurt again and never blistered.

Example X: Ringworm on a Bull

A rancher complained of a problem causing his bull to scratch himself continuously to the exclusion of all activity other than eating and drinking. A veterinarian examined the bull and determined that the bull had an extensive case of ringworms, a fungal infection. The rancher was given 8 ounces of the salve in Example 4, and was told to dilute it with two gallons of water and spray it thoroughly over all of the bull's skin with a garden sprayer. An inquiry a week later revealed that all signs of the infection were gone and the bull was no longer scratching.

Example XI: Jellyfish Sting

A 21 year old Caucasian female received two vertical jelly fish stings about 0.2 cm wide and 30 cm long down her right leg. The patient complained of a continuous severe pain. After 10 minutes, the stings were treated with the salve in Example 4. A generous amount of salve was applied to the sting and the area was massaged vigorously adding more salve when the area started to get sticky. Continued massaging of the area was done until the stinging started to abate. After 30 minute the pain was gone. After that time, all discomfort had ceased, and the red stripes had started to fade. After two weeks, the red stripes were gone.

Example XII: Fire Ant Stings

A 6 year old Caucasian girl was stung by fire ants 23 times on the right ankle and calf. The mother quickly administered a generous amount of salve in Example 4 and vigorously massaged the whole area of the stings until the stinging ceased, a period of about 3 minutes. Subsequent to the treatment, the stings did not develop into pustules as would normally happen.

Example XIII: Poison Ivy

A 35 year old Caucasian female developed large patches of contact dermatitis from poison ivy on both forearms and her right cheek. Severe itching and pain continued for three days, interfering greatly with the patient's work and nightly rest until the lesions were treated with the salve in Example 4. Immediately, the pain and itching subsided, prompting the patient to say that the salve was "paradise in ajar". Itching recommenced after bathing, so treatment was restarted at intervals for the next two days. After that period, the lesions had stopped itching, and the redness had diminished. After about a week, all signs of the dermatitis were gone.

Example XIV: Canine Contact Dermatitis

A white, 5 year old miniature poodle had two patches of contact dermatitis (hot spots) as roughly circular 3 cm lesions on the upper right side of the back, and a roughly circular 2.5 cm lesion on the inside of the left front leg. Both lesions had been scratched and gnawed by the dog until they were slightly bloody. Both lesions were treated with salve in Example 4. The fur was cut short with clippers and the salve was massaged into the lesions. The owner was given a jar of the salve and given application instructions. The dog licked the salve off of the lesions on two different occasions, but salve was always reapplied. After that reapplication the dog left them both medicated. Treatment continued once daily for three days. The poodle never recommenced scratching and gnawing of the lesions. No side effects were observed from ingestion of the salve. The lesions did not reoccur.

Example XV: Canine Ear Infection

A 7 year old black Labrador Retriever was taken to the veterinarian to get his ears treated for ear infections. The ears were inspected and found to have both fungal and bacterial infections. Each ear received 2 mL of salve of Example 4. Each ear was then massaged so as to encourage movement of the salve down the ear canal to the ear drum. The owner was given a bottle of the salve, an ear syringe, and instructions for salve application. Each ear was washed gently, but thoroughly, each morning with distilled water using the ear syringe to remove any residual solids. Then, each ear again received an injection of the salve into the ear canal. On the third day, the ears were both washed thoroughly with distilled water using the ear syringe, then inspected and found to be infection free. No further injections of salve were made.

Example XVI: Multiple Lesions Inside of the Mouth

A 78 year old Caucasian female had multiple lesions inside of her mouth. The pathogens responsible for the lesions were never determined, but were assumed to be herpes simplex. She had received multiple different remedial treatments from her dentist to no avail. She was given a jar of the salve of Example 4, and told to vigorously swish the salve in the mouth for three minutes morning and night. After 7 days, all the lesions had completely healed.

Example XVII: Uterine Infection of a Mare

A seven year old quarter horse mare had successfully foaled but was found to have subsequently acquired a severe uterine infection. She was brought to the veterinarian for treatment. A swab revealed that her uterus was infected with *E. coli* bacteria. An 8 mL syringe of the salve of Example 4 was injected through the cervix into the uterus. Two days later swabs taken from the uterus that revealed no infection.

Example XVIII: Skin Bruises

An 82 year old Caucasian male had bruised the top of his left arm leaving a dark brown, unsightly bruise about 5 mm wide and 5 cm long. Each morning the surface of the bruise was washed with soap and water, then salve in Example 4 was applied. The dried film was left in place until the next application. The color of the bruise gradually diffused outward to a distance of about 1 cm from the initial bruise while becoming less visible. After ten days, the bruise had disappeared.

Example XIX: Gingivitis Infections in Canines

A 5 year old Cocker Spaniel was brought to the veterinarian to get treatment for a mouth severely infected with gingivitis. The mouth was thoroughly swabbed with salve in Example 4. The treatment was repeated once again the following day. All signs of the infection disappeared.

Example XX: Prophylactic Use to Prevent Formation of Lesions on the Legs of a Diabetic A 72 year old Caucasian woman had repeatedly suffered the outbreak of lesions on her legs caused by type 2 diabetes. She started using daily applications of the salve in Example 4 to both legs. All lesions were healed within two weeks and no more lesions occurred as long as she continued the application of the salve.

Example XXI: Methicillin Resistant *Staphylococcus aureus*

A 4 year old quarter horse mare had received a 4 inch cut on the chest from an encounter with a corral fence and had developed an infection. The wound was first treated with nitrofurazone ointment but after two days with no positive result, the horse was given a 10,000 units per pound body weight injection of penicillin. The horse was examined again after 72 hours, and no improvement was again noted. At that time, a specimen was taken from the wound and sent to a diagnostic lab for identification. Treatment of the wound was then started with silver sulfa diazole. When the results were returned from the diagnostic lab, the pathogen was identified as methicillin resistant *Staphylococcus aureus*. At that time, salve as described in Example 4 was applied to the wound, and then reapplied twice daily. Improvement was observed by the next day and treatment continued. After three days there was no evidence of infection. After five days, the wound had closed and treatment was discontinued.

Example XXII: Wound Healing for a Horse

Since the anion exchange capacity of the microcrystals is presented in ever increasing concentration, the film acquires more and more affinity for some allergens, an attribute for treating allergic contact dermatitis. The film shrinks as it dries, and this seems to contribute to a palliative effect perhaps due to reduced tension on the nerves in the skin. No bandages were needed to be applied—important for a horse to prevent it from trying to gnaw or rub off the bandage. This result from the application of the MMOH formulation of Example 4 to the horse of Example VIII having a very severe injury is shown by the following photographs:

FIG. 1 is the initial intake of the horse with the injury by the veterinarian (time I). FIG. 2 is 45 days from time I. FIG. 3 is 75 days from time I. FIG. 4 is 90 days from time I. The lighting was not controlled for these pictures. The horse fully recovered.

Example XXIII: Contact Dermatitis Lesion of a Golden Retriever Male Dog

Figure 7A:
FIG. 7A is a photograph of a male dog with a large abraded contact dermatitis lesion on its right hip.
Figure 7B:
FIG. 7B is two weeks after the lesion was treated; the dog fully recovered with hair grown back.

A neutered male dog (13 years old, 92.3 lbs.) with a large abraded contact dermatitis lesion was treated for the purposes of getting before and after blood samples to show the salve does not become systemic. FIG. 7A is from this dog viewing the back right of the dog to show the severe lesion. When the dog was brought in for treatment, he was gnawing this area often. FIG. 7B shows the dog after treatment. The veterinarian stated that the dog is no longer gnawing at the area because there is no itching and the hair is growing back and the infection is gone.

The lesion on the dog was cured after several treatments with the present salve and the microcrystals did not go into the blood stream. This is shown by the results from the testing by blood draws for magnesium done by the veterinarian both before and after treatment in the dog.

Serum draws were taken and analyzed for Mg by Texas A&M Veterinary Medical Diagnostic Laboratory—summary of their report provided with permission. Prior to any treatment the Mg level in the dog was 1.6 mEq/L. After treatment of the lesion with the present salve the Mg level was 1.6 mEq/L. Thus, no change in the blood level of Mg which was present in the MMOH salve.

As can be seen from this report there was no difference in these results such that the levels did not go up as would happen if the MMOH was in the blood stream.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A formulation consisting of a mixed metal hydroxide, MMOH, of the formula

$$(Li)_z D_d T(OH)_q (A^{-1})_y \cdot xH_2O \quad \text{Formula (I)}$$

wherein:
D is a divalent metal of Mg, Ca, Zn, Mn, Co or Ni;
d is 0.8 to 1.1 and can be other than an integer;
T is a trivalent metal of Al or Ga;
A is an anion of Cl, Br, F or I;
is 0 to 0.4, and can be other than an integer;
q is 4.6 to 5.7, and can be other than an integer;
z is 0 or 1, and can be other than an integer;
   $xH_2O$ is water of hydration, entrapped or associated with the MMOH crystal lattice, where x is from 6 to 100;
with an aqueous, non-anionic, nontoxic thickener, which does not destroy the crystalline structure of the MMOH, selected from Cellulosic thickeners,
wherein the ratio of MMOH to thickener is about 2/3 by wt. MMOH to 1/3 by wt. thickener,
to form an aqueous, nontoxic adduct as a salve or lotion that is resistant to syneresis.

2. The formulation of claim 1 wherein D is Mg, and T is Al.

3. The formulation of claim 2 wherein the ratio of Mg:Al is 0.82.

4. The formulation of claim 2 wherein A is Cl.

5. The formulation of claim 1 wherein q is 4.7 and y is 0.3.

6. The formulation of claim 1 wherein the salve does not agglomerate or separate into two phases.

7. The formulation of claim 1 wherein the thickener is hydroxypropyl methyl cellulose (HPMC) or methyl cellulose (MC).

8. The formulation of claim 1 wherein the aqueous thickener has a pH of between 6 and 9.

9. The formulation of claim 1 wherein the salve or lotion forms a film after applying which shrinks upon drying and is an astringent.

10. A method of treating a person or an animal having need of a topical treatment for damage to the outer surface of their body using a salve or lotion of Formula (I) as defined in claim 1.

11. The method of claim 10 wherein the applied formulation dries as a film, is nontoxic, an astringent, reduces infections from germs, viruses, bacteria, fungus, yeast, or any microscopic organism which has a negatively charged surface.

12. The method of claim 11 wherein the damage to the animal or person requiring treatment is caused by one or more of the following:
   a) wounds, rashes, and lesions from becoming infected
   b) bruises or subcutaneous hematomas to dissipate and disappear
   c) burns and blisters to heal without infection, including any lesions
   d) proud flesh prevention as wounds heal
   e) itching and discomfort to disappear and rashes causes by poison or allergens to dissipate caused by poison ivy, poison oak, and poison sumac; shingles; eczema; mosquitos and chiggers; and contact dermatitis lesions
   f) pain and blisters of insect stings or bites, from any source that causes such pain or blisters, or jelly fish stings, and
   g) pain relief from sunburn or painful irritation from exposure to chemicals and allergic reactions of the skin.

13. The method of claim 10 wherein the formulation sequesters allergens that cause inflammation or infections.

14. The method of claim 10 wherein the formulation reduces various skin maladies by removing skin tags; small warts; seborrheic keratoses; or toenail fungus.

15. The method of claim 10 wherein the formulation does not enter the blood stream but provides treatment for infections by any negative pathogen of the mouth, uterus, urinary tract, or ears.

16. The method of claim 10 wherein daily application of the formulation causes hemorrhoids to dissipate.

17. The method of claim 10 wherein the formulation is capable of effectively killing pathogens which are deemed to be antibiotic resistant and wherein the pathogen cannot develop a resistance to the formulation.

* * * * *